US007587105B2

(12) United States Patent
Ashkenazi et al.

(10) Patent No.: US 7,587,105 B2
(45) Date of Patent: Sep. 8, 2009

(54) HIGH FREQUENCY ULTRASOUND DETECTION USING POLYMER OPTICAL-RING RESONATOR

(75) Inventors: Shai Ashkenazi, Ann Arbor, MI (US); Lingjie Jay Guo, Ann Arbor, MI (US); Matthew O'Donnell, Ann Arbor, MI (US)

(73) Assignee: The Regents Of The University Of Michigan, Ann Arbor, MI (US)

( * ) Notice: Subject to any disclaimer, the term of this patent is extended or adjusted under 35 U.S.C. 154(b) by 23 days.

(21) Appl. No.: 11/662,154

(22) PCT Filed: Sep. 8, 2005

(86) PCT No.: PCT/US2005/031905

§ 371 (c)(1),
(2), (4) Date: Mar. 7, 2007

(87) PCT Pub. No.: WO2007/018552

PCT Pub. Date: Feb. 15, 2007

(65) Prior Publication Data

US 2008/0095490 A1    Apr. 24, 2008

Related U.S. Application Data

(60) Provisional application No. 60/607,982, filed on Sep. 8, 2004.

(51) Int. Cl.
*G02B 6/00* (2006.01)
(52) U.S. Cl. .................................................. 385/13
(58) Field of Classification Search .................... 385/7, 385/13, 30, 32, 50
See application file for complete search history.

(56) References Cited

U.S. PATENT DOCUMENTS 5,091,983 A * 2/1992 Lukosz ........................ 385/13
7,526,148 B2 * 4/2009 Kilic et al. ................... 385/12

* cited by examiner

*Primary Examiner*—Sarah Song
(74) *Attorney, Agent, or Firm*—Harness, Dickey & Pierce, P.L.C.

(57) ABSTRACT

A polymer waveguide resonator device for high-frequency ultrasound detection having a optical resonator coupled to a straight optical waveguide which serves as input and output ports. Acoustic waves irradiating the waveguide induce strain modifying the waveguide cross-section or other design property. As a consequence, the effective refractive index of optical waves propagating along the ring is modified. The sharp wavelength dependence of the high Q-factor resonator enhances the optical response to acoustic strain. High sensitivity is demonstrated experimentally in detecting broadband ultrasound pulses from a 10 MHz transducer.

26 Claims, 10 Drawing Sheets

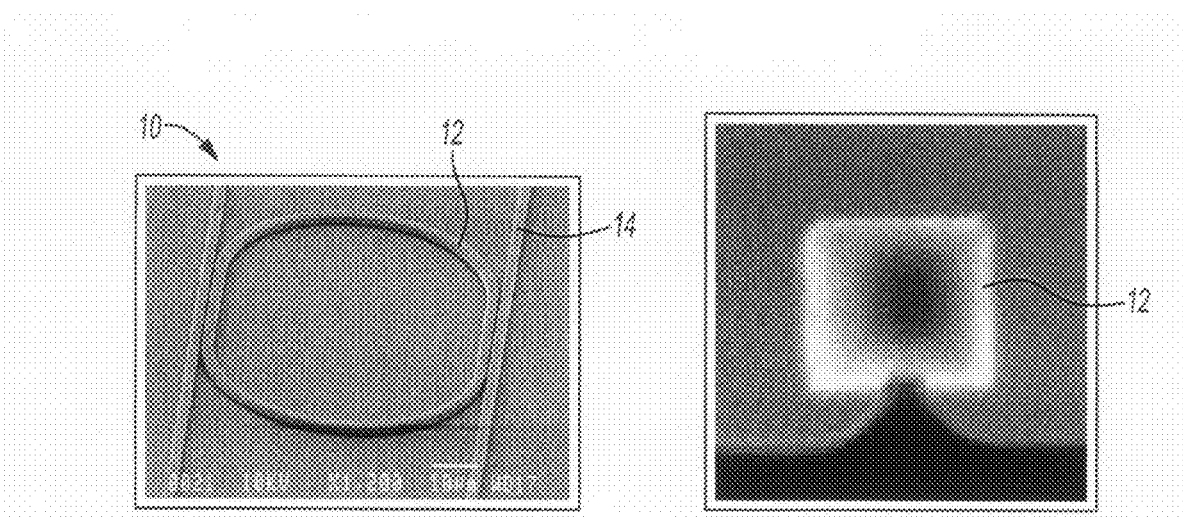
*Fig-5*
*Fig-6*
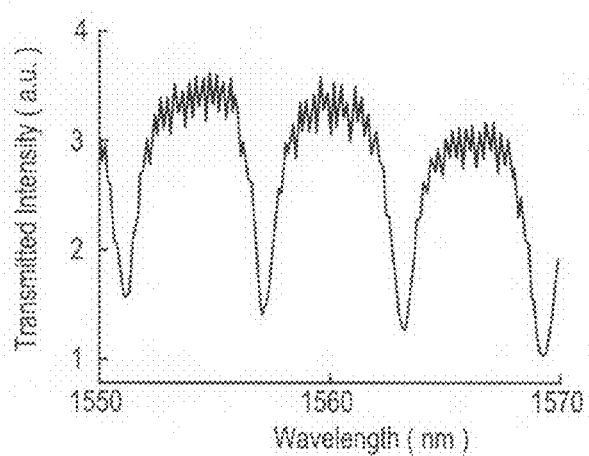
*Fig-7a*
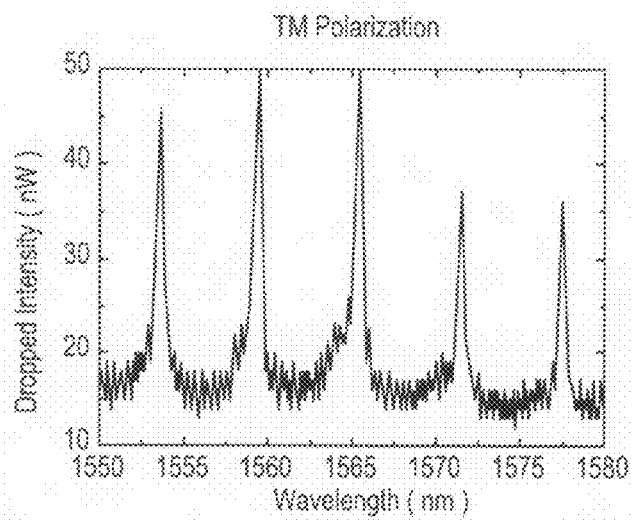
*Fig-7b*

HIGH FREQUENCY ULTRASOUND DETECTION USING POLYMER OPTICAL-RING RESONATOR

CROSS-REFERENCE TO RELATED APPLICATIONS

This application claims the benefit of U.S. Provisional Application No. 60/607,982, filed on Sep. 8, 2004. The disclosure of the above application is incorporated herein by reference.

GOVERNMENT RIGHTS

This invention was made with government support under Grant Nos. HL47401 and EB007619 awarded by the National Institutes of Health. The government has certain rights in the invention.

FIELD

The present teachings relate to ultrasound detection and, more particularly, relate to high frequency ultrasound detection using polymer optical-ring resonators.

BACKGROUND AND SUMMARY

Detection of ultrasound using optical techniques has gained increasing interest during recent years. Resonant optical structures, such as etalons, fiber gratings, and dielectric multilayer interference filters, can be employed as ultrasound sensing elements. These devices rely on the interaction of an optical field confined in a resonance cavity with a transient ultrasonic field. The interaction takes place due to the modulation of the optical properties of the resonance cavity in response to the strain induced by the ultrasonic field. The sharp resonance line of the cavity amplifies the optical response to the transient strain. The advantage of using optical methods over conventional piezoelectric based sensors is apparent when small element size ultrasound arrays are considered. The effective area of an optically based ultrasound sensor is determined by the size of the confined optical field, which in most cases can be scaled down to micrometer size without increasing detection noise. For the case of a piezoelectric sensing element, however, signal noise increases with reduced element size.

Microresonator detectors can rely on accurate measurement of the effective refractive index change of the guided mode inside waveguides, due to the presence of biomolecules on the surface of sensing areas or in the solution surrounding the devices. In microresonator detectors, signals can be detected by measuring resonance shifts, or alternatively, by measuring output intensity changes from the device at a fixed wavelength. The latter technique is especially useful for detecting very small changes in the effective index. Such a property can be used to detect, sensitively, the resonator's response to an incident ultrasound pulse. Accordingly, this arrangement can be used for high-frequency ultrasound detection. Moreover, ultrasound imaging with high-spatial resolution can be achieved using arrays of integrated microring resonators.

Very high frequency ultrasound imaging at the frequency range of 30-100 MHz is capable of resolving structures almost down to the cellular level. Developing such an imaging modality for clinical use could have a tremendous impact on the diagnostic and therapeutic procedures in many different clinical areas. The cardio-vascular clinician will be able to visualize in great detail the arterial walls of the coronary arteries and the heart interior structure. The diagnostics of cancer using biopsy will be revolutionized as in-situ microscopy could replace the traditional procedure. Imaging guided therapy could be developed since the diagnosed pathology can be localized at a great precision.

Currently intravascular ultrasound (IVUS) imaging is used in arterial wall imaging for cardiovascular diagnostics. The resolution attained by these devices exceeds 100 µm (more than 200 µm laterally). Due to their limited resolution current IVUS devices are unable to show early stages of atherosclerosis, or to identify thin fibrous caps, a hallmark of plaques believed to be most susceptible to rupture.

According to the principles of the present teachings, a method is provided that is based on optical microresonators of very high quality factor acting as highly sensitive ultrasound receivers. These microresonators, designed using integrated optics techniques, are formed using closed-loop (ring type) shaped waveguides. A typical dimension of such a microresonator is 20 µm to 60 µm depending on the optical wavelength and other design parameters. Preliminary measurements showed an extraordinary high sensitivity giving rise to a high signal to noise ratio of about 30 using a driving acoustic signal of 60 KPa power. These experiments were performed using a microring resonator of moderate quality factor (Q=1000) excited using relatively low optical power of 1.5 mW. These results imply that a microring array having an element spacing of less than 20 µm could deliver high sensitivity and provide image resolution that is at least five times better that of any existing IVUS system. Such a system can utilize separate optical elements acting as ultrasound generators whose principle relying on photoacoustic ultrasound generation.

The design of a 1-D or 2-D microring array using integrated optics device techniques according to the present teachings offers unique advantages such as ruggedness, small size, RF immunity, and low manufacturing cost, which could be beneficial in various ultrasound applications. A particularly appealing medical application is the design of a small integrated optical device which will operate as an intravascular imaging probe. The ultrasound pulse generator could be integrated using photoacoustic methods, therefore eliminating the need for any electrical cabling since fiber optics carry both input and output signals. The high element density required for high resolution intravascular imaging dictates an upper limit on the ring diameter. Reducing the size of the rings will also increase the free spectral range and therefore will increase the number of elements that can share a common bus waveguide.

Further areas of applicability of the present teachings will become apparent from the detailed description provided hereinafter. It should be understood that the detailed description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein.

DETAILED DESCRIPTION

Figure 1:
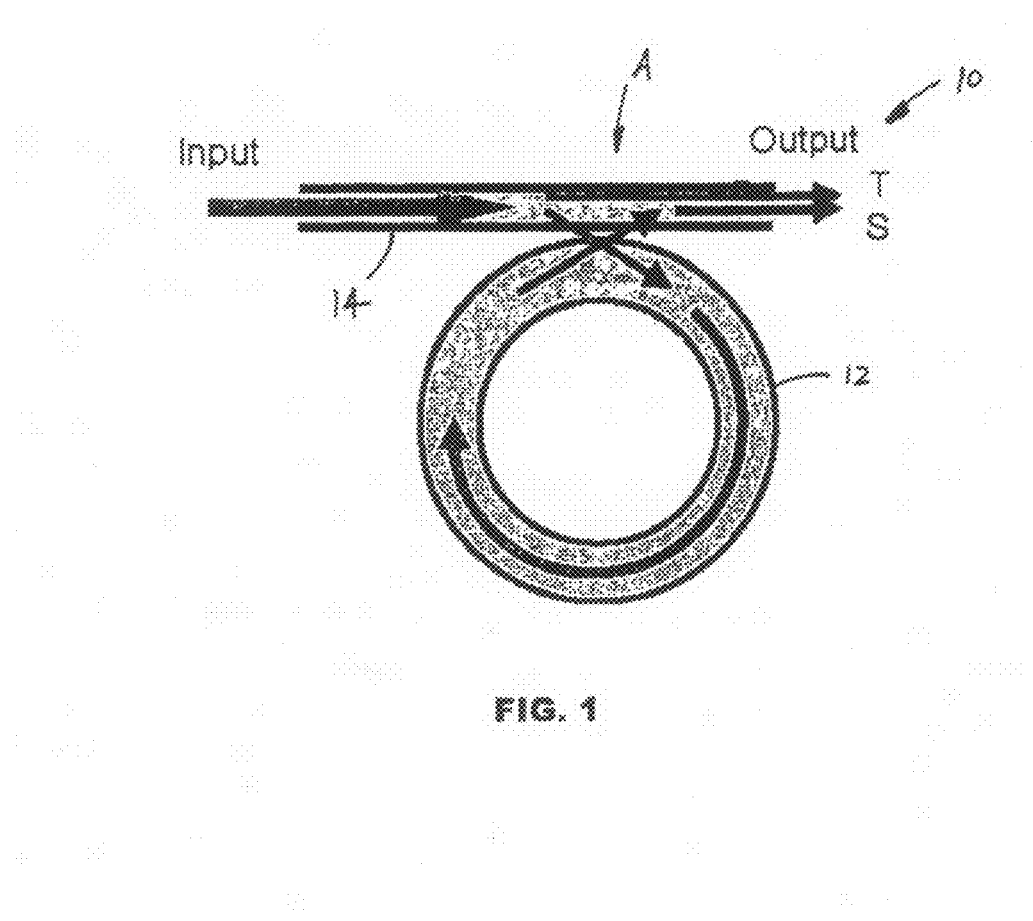
FIG. 1 is a schematic view illustrating a microring resonator according to the principles of the present teachings.

The following description of the preferred embodiments are merely exemplary in nature and is in no way intended to limit the present teachings, its application, or uses.

The present teachings are believed to boost optical detection of ultrasound from the current experimental system carried out on an optical table to a compact and robust device that is perfectly suitable for interventional imaging application. The integrated optics concept and the novel implementation of photonic microresonators as ultrasonic detectors are the corner stones of the present teachings.

From a medical perspective, the greatest impact of the present teachings would be on the treatment of cardio-vascular diseases. A device based on the present teachings can feature one or more of the following:

1. High-resolution imaging revealing detailed structures such as the thin fibrous cap covering vulnerable plaque.

2. High image contrast obtained by realizing several imaging modalities on the same device. These modalities include:
   a. Ultrasonic pulse/echo imaging
   b. Photoacoustic imaging revealing optical properties of the tissue structure.
   c. Elasticity imaging differentiating tissue components by their elastic properties.
   d. Thermal imaging shows differences in thermal properties of the tissue.

3. Low cost manufacturing technique using polymer imprinting methods facilitates a disposable probe.

From a technological perspective, the present teachings bring innovation in two of its basic aspects:
   a. Optical microresonators can be used as high-frequency ultrasound detectors for the first time; and
   b. An array of microresonators can be used for wavelength division multiplexing (WDM).

Technological Environment

Intravascular Imaging

Intravascular ultrasound imaging is a powerful tool for cardiovascular diagnosis and treatment guidance. In clinical practice, IVUS is most often used as an adjunct to balloon angioplasty (catheter based procedure performed to open clogged coronary arteries using a balloon, usually including placement of a metal stent for the fixation of the artery wall). IVUS imaging guides the procedure and assists in monitoring the proper stent deployment. IVUS guiding reduces potential complications such as stent thrombosis and restenosis. IVUS imaging is also beneficial in guiding atherectomy procedures (the removal of plaque from arterial walls using a blade or laser plaque melting) which in many cases precede balloon angioplasty or stenting. IVUS has also been investigated as an initial technique to determine plaque composition, and thus guide selection of a potential revascularization technique, i.e., atherectomy, angioplasty, and/or stent placement.

Current IVUS devices use piezoelectric technology. The accumulated clinical experience in employing IVUS imaging for cardiovascular diseases diagnosis and treatment reveals two major limitations of these devices. First, image resolution is not adequate for detecting early stages of arterial pathology (intimal thickening) or the thin fibrous cap enclosing a lipid plaque. In addition, on far many cases, image contrast, based on the difference in ultrasound reflection properties, does not identify lipid based plaque.

These limitations initiated intensive search for alternative imaging methods employing different contrast mechanisms. Methods based on optical properties imaging such as OCT and fiber optic spectroscopy are investigated. Optical properties can probe the chemical composition of the tissue and therefore provide enhanced differentiation of arterial wall tissue and lipid pools within the arterial wall. OCT images have excellent spatial resolution in the order of 10 mm. The drawbacks of OCT are long frame acquisition time and multiple scattering due to red blood cells which requires flushing of blood with clear saline. Other methods suggested different plaque identifying mechanisms. Ultrasound elasticity imaging can map the elastic deformability of tissue. The lipid plaque pool is much more deformable than the surrounding arterial wall, and therefore will show up clearly in elasticity based imaging. A combination of acoustic and thermal properties is the basic contrast mechanism for a newly introduced technique of thermal imaging. The differentiating parameter in this technique changes sign between water bearing tissue and lipid due to the opposite dependence of sound velocity on temperature. High contrast was demonstrated in thermal imaging on in-vitro tissue samples. Both of these ultrasound based technologies improve the image contrast on the expanse of reducing the spatial resolution.

Optical Detection of Ultrasound

The requirement for higher resolution ultrasound scanners led to the development of miniaturized piezoelectric imaging probes. The small element size and high element density pose major fabrication challenges however, for piezoelectric arrays. The transmission of the electrical signal from the active piezo-element to the instrument base is another source of difficulty due to the relatively large noise level and high loading of the transmission line. State of the art catheter based ultrasonic array operates at a maximal frequency of 20 MHz.

Addressing the above issues of high frequency piezoelectric arrays accelerated the development of alternative ultrasound transduction technologies. Capacitive transducers have been investigated for several decades. The recent advances in microfabrication techniques have enabled capacitive transducers rivaling piezoelectric equivalents. The capacitive micromachined ultrasound transducer (cMUT) developed by Khuri-Yakub and his group at Stanford has challenged many assumptions about non-piezoelectric transduction for biomedical applications. High transduction efficiencies can be obtained with these devices; large element count arrays can be fabricated using standard silicon processing technology; and significant bandwidths are possible. Although very attractive for low frequency, in high element count arrays, individual electrical connections must still be made to each element. In addition, high-frequency operation requires a dedicated, high bandwidth preamplifier integrated with each element. For high-frequency applications with large element counts, there is still great need for an alternate transduction technology.

Optical techniques to detect and generate ultrasound have been suggested for high frequency transducer arrays. Several optical methods have been devised to detect ultrasound. The simplest optical detector element is a reflecting surface. Ultrasonically induced surface displacement modulates the phase of an optical beam reflecting off the surface. Interferometric techniques are then applied to demodulate the phase information reconstructing the ultrasonic displacement signal. The size of the active detector element is determined by the optical spot size of the beam. Focusing the beam to a few wavelengths spot size enables ultrasound detection with an element size of several micrometers. Multipoint detection (array detector) has been demonstrated by scanning the optical beam over the effective array aperture. A major drawback of this scheme is low detection sensitivity. Since typical ultrasonic displacements are much smaller than the optical wavelength (4 to 5 orders of magnitude), optical modulation is weak resulting in low detection sensitivity.

Another approach for optical detection of ultrasound is based on a Fabry-Perot etalon as the active detector element. An etalon is an optical resonator structure consisting of a transparent material slab coated with semitransparent mirrors on both sides. A Resonance condition occurs whenever the multiple reflected beams from the etalon are in-phase. The thickness of the etalon determines the resonance wavelength. Ultrasonic waves traveling through the etalon or reflecting from one of its surfaces modulates the thickness of the etalon and therefore shifts the resonance wavelength. The intensity of a reflected beam from the etalon is modulated by the resonance shift provided that the wavelength of the reflected beam is chosen to be at the steep edge of the resonance curve. High sensitivities have been demonstrated using etalon based ultrasound detection.

Optical Generation of Ultrasound

Laser pulses of short duration (typically a few nanoseconds) hitting an absorbing material will induce transient heating followed by a rapid pressure change. The effect is termed photoacoustics. High bandwidth (>100 MHz) ultrasound spikes can be generated using photoacoustics. Photoacoustics emerged during the recent decade as a valuable new modality in medical imaging. The use of photoacoustics in medical imaging can be categorized into three main modes. The first exploits photoacoustic ultrasound generation in a highly absorbing material (usually not the tissue) to form highly localized acoustic source. The acoustic waves of the photoacoustic source are then propagating through the tissue while a separate ultrasonic receiver is used to detect the backscattered waves. Thus, in this mode, the photoacoustic source replaces the traditional piezoelectric source. The second mode allows the laser radiation to be absorbed within the tissue structure. The light absorbance in the tissue creates an extended ultrasound source having a spatial amplitude distribution which reflects the inhomogeneity of the optical properties (absorption) of the tissue structure. The ultrasound field created by this extended source is detected and reconstruction algorithms are employed to form an image which maps the optical absorption of the tissue. The images therefore depend on the laser wavelength and shows sensitivity to the chemical composition of tissue components. The third mode is similar to the second except that a high optical absorption contrast agent or a specific molecular tagging agent is administered to the imaging location. The image shows the distribution of the specific contrast agent used.

Microring Photonic Resonators

Figure 2:
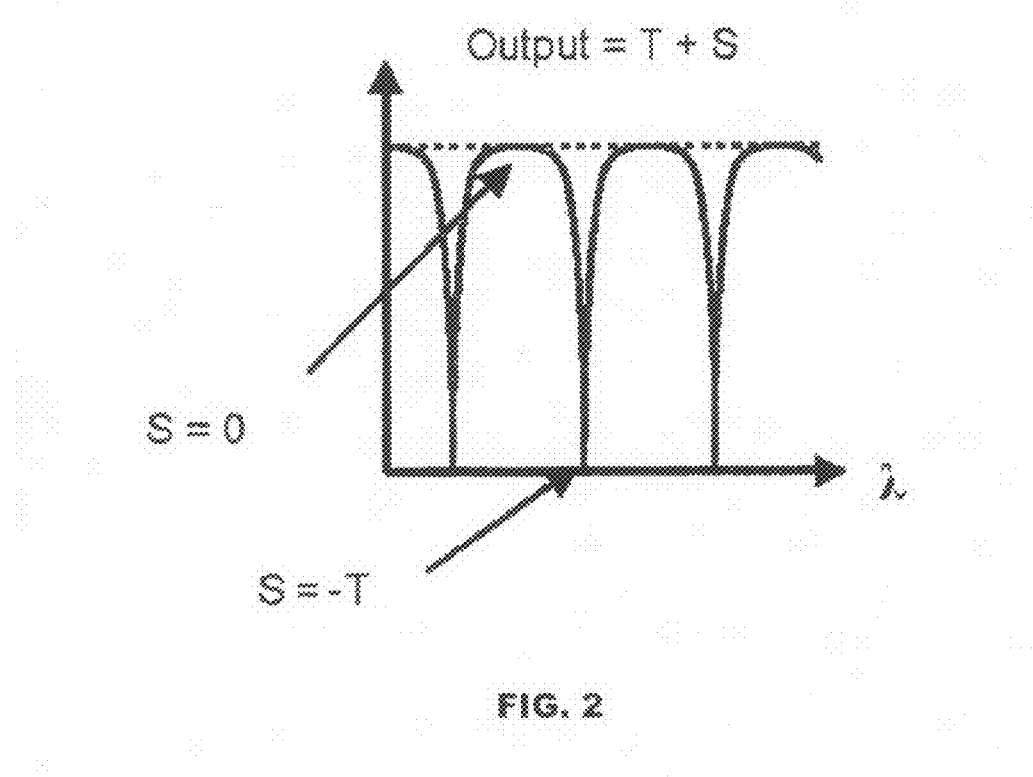
FIG. 2 is a graph illustrating a resonance spectrum of the microring resonator of FIG. 1.

As is described and illustrated herein, high frequency ultrasound receiver elements can be realized using a high Q-factor microring resonator device. As illustrated in FIG. 1, a microring resonator device 10 is provided having a closed-loop waveguide or ring resonator 12 and a straight or bus waveguide 14 that couples light in and out of ring resonator 12. The coupling is generally confined to a region, generally indicated at A, where the light distributions at the two waveguides significantly overlap. It should be appreciated, however, that ring resonator 12 may have various configurations and shapes, such as disc, rectangular, spherical, and the like. Optical resonance occurs at multiple wavelengths $\lambda_m$ satisfying the condition $m\lambda_m/n_{eff}=L$, where m is a positive integer, $n_{eff}$ is the effective refraction index for the guided mode along ring resonator 12 and L is the circumference of ring resonator 12. The effective refraction index depends on the polarization of the light, the geometry of straight waveguide 14, and on the bulk refraction indices of the waveguide material and the surrounding media (cladding). Under such condition, it can be shown that the field of the optical wave, S, returning to the coupler (i.e. region A) after a round trip about ring resonator 12 is exactly $\pi$ out of phase with the optical wave, T, traveling through the coupler region A in straight waveguide 14. These two fields therefore interfere destructively. As seen in FIG. 2, a schematic representation is illustrated of the optical fields in microring resonator 10. After a round trip, if the fraction of field remaining after the propagation loss, a, matches the transmission coefficient in the straight waveguide, T, the amplitudes of the two fields are equal leading to a complete destructive interference and a zero intensity at the output port of the bus waveguide. The condition $a=|T|$ is referred to as critical coupling condition.

Figure 3:
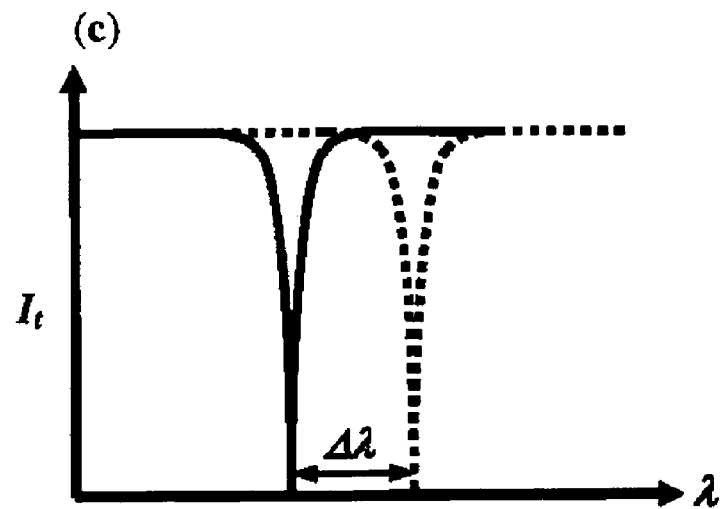
FIG. 3 is a graph illustrating a resonance shift in response to an externally applied strain.

The resonant wavelengths are highly sensitive to the effective index change of the guided mode. This characteristic will be used to implement sensitive ultrasound detectors. Ultrasound waves stress the complex waveguides structure deforming both the ring waveguide and the coupling region. These deformations (i.e. strain) induce a wavelength shift, as illustrated in FIG. 3, in the resonance structure denoted by Δλ. Amplified modulation of the transmitted light at a fixed wavelength can be obtained by choosing a wavelength at the steep edge of the transmission spectrum.

Figure 5:
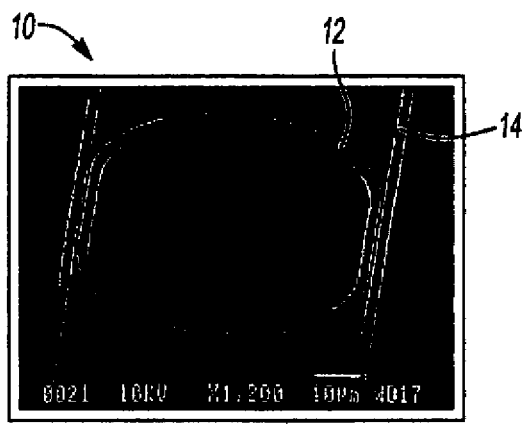
FIG. 5 is a SEM picture of a perspective view of the microring resonator according to the present teachings.
Figure 6:
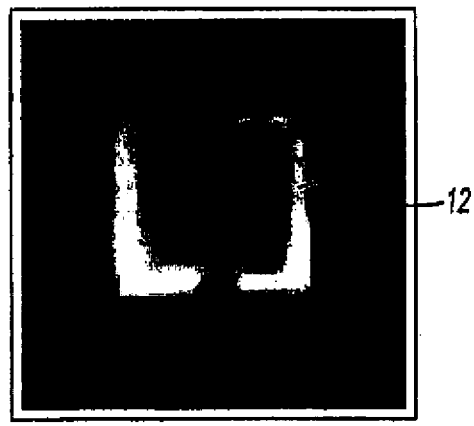
FIG. 6 is a SEM picture of a cross-sectional view of the microring resonator according to the present teachings.

According to the principles of the present teachings, a polystyrene (PS) waveguide structure, consisting of a closed-loop, racetrack-shaped resonator coupled with a straight waveguide was fabricated on a silicon substrate using an imprinting technique. In order to test the device, the device was fabricated and ultrasonically irradiated while performing optical transmission measurement. The resonator diameter (of the two semicircles) is 60 μm and its cross-section dimension is 2.3 μm×1.8 μm. FIG. 5 illustrates a scanning electron microscope (SEM) image of the device having a cross-sectional configuration as illustrated in FIG. 6. The transmission spectrum of the device was measured using a tunable laser (Santec TSL-220) spanning the range of 1530 nm-1610 nm at 1.5 mW output power. The polarization of the input beam was controlled using a half-wave plate and a polarizer. The laser beam was coupled into the waveguide and collected by objective lenses. The measured transmission spectrum, using deionized water as cladding material, is shown in FIG. 5. The resonator has a moderate Q of 1000.

Microring Detector

Figure 4:
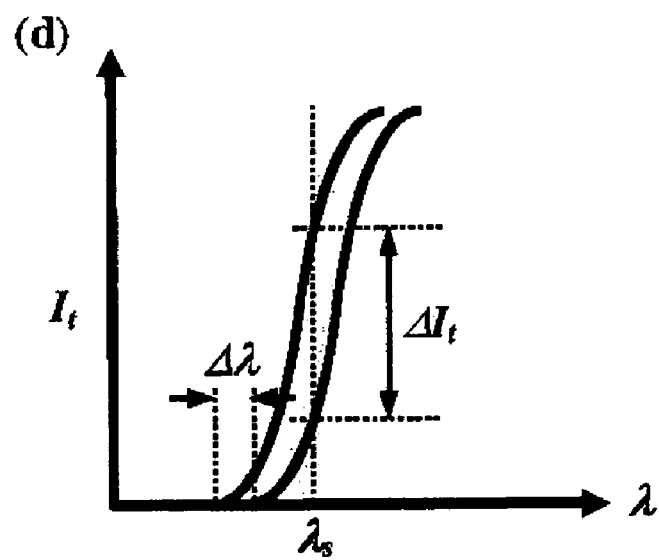
FIG. 4 is a graph illustrating an intensity variation at a fixed wavelength, $\lambda_s$, with respect to a chance in the effective refractive index.

Microresonators can also be used as detectors because their resonances can respond sensitively to the change in the effective refractive index of the guided optical mode. For example, microring devices have been considered for label-free biosensor applications, where the effective index change is caused either by the presence of biomolecules attached on the surface of sensing areas, or by the refractive index change of a solution surrounding the devices. It has been estimated that effective refractive index resolution down to $10^{-9}$ should be feasible by using high-Q microresonators. In microresonator detectors, detections can be made by measuring the resonance shifts (FIG. 3); or alternatively, by the measurement of the output intensity change from the device at a fixed wavelength (FIG. 4). The latter scheme is especially useful for detecting very small change in the effective index, and our preliminary results show that such a property can be used to detect, sensitively, the polymer response to an incident ultrasound pulse. We propose that this scheme is the preferred technique for high-frequency ultrasound detection; and when combined with arrays of integrated microring resonators, capable of ultrasound imaging with high-spatial resolution.

Polymer Microrings

The use of polymers in the present teachings provide advantages, such as the ability to attenuate interfaces and mode conversions from longitudinal waves to surface waves and sheer waves. Such features can increase the imaging bandwidth and reduce the crosstalk between elements in imaging arrays. Polymers also provide the advantages of low cost, easy processing; high compatibility with different substrate systems and therefore easy integration. Furthermore, for the microring waveguide devices, the use of polymer materials offers several other attractive features over semiconductor-based devices, including reducing surface roughness induced loss that limits the Q-factor of the resonators, providing better coupling efficiency to optical fibers, which will greatly facilitate the device integration and characterization.

Device Fabrication

Figure 7A:
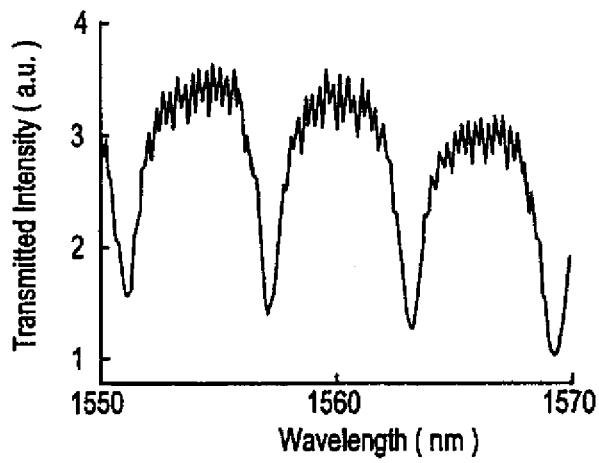
FIG. 7(a) is a graph illustrating the optical transmission spectrum of a microring device.
Figure 7B:
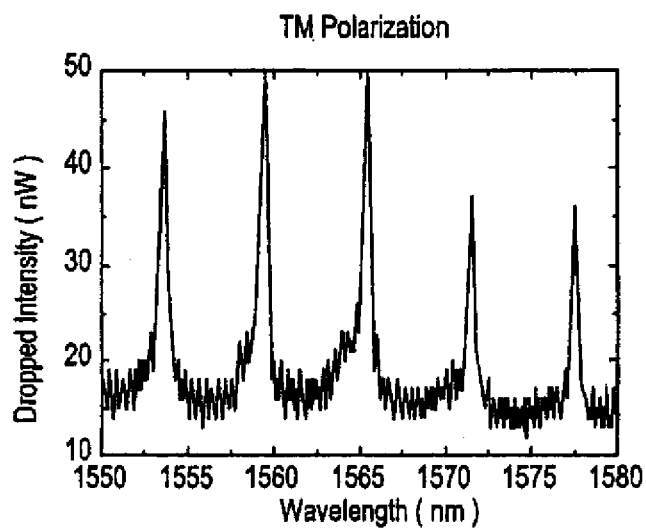
FIG. 7(b) is a graph illustrating the optical spectrum measured from the drop port of a microring resonator.
Figure 8:
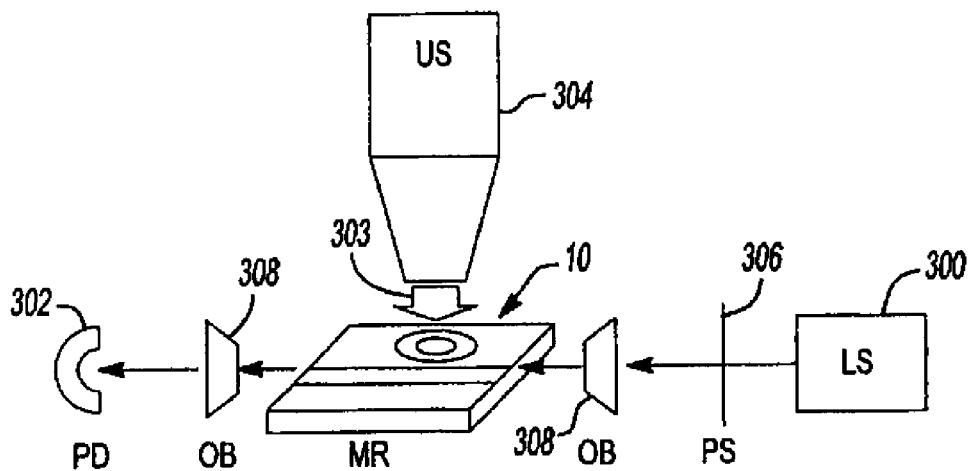
Figure 9:
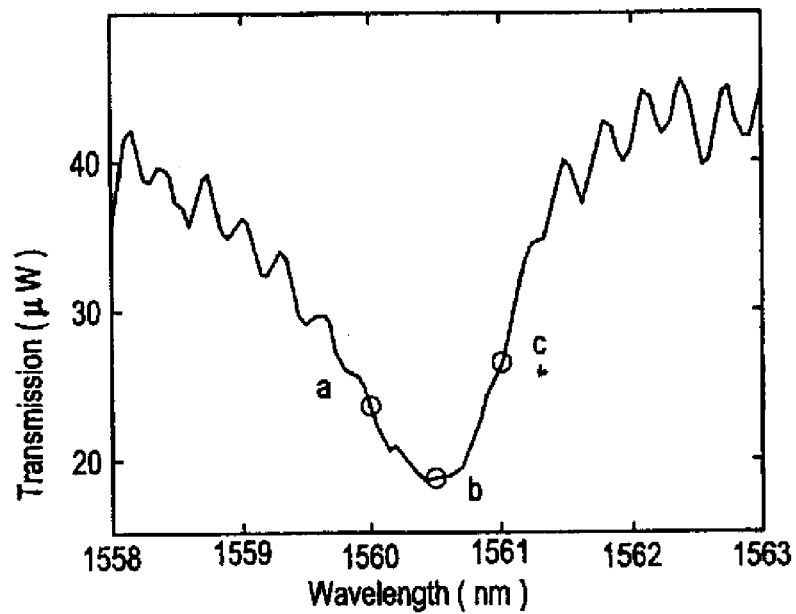
Figure 10A:
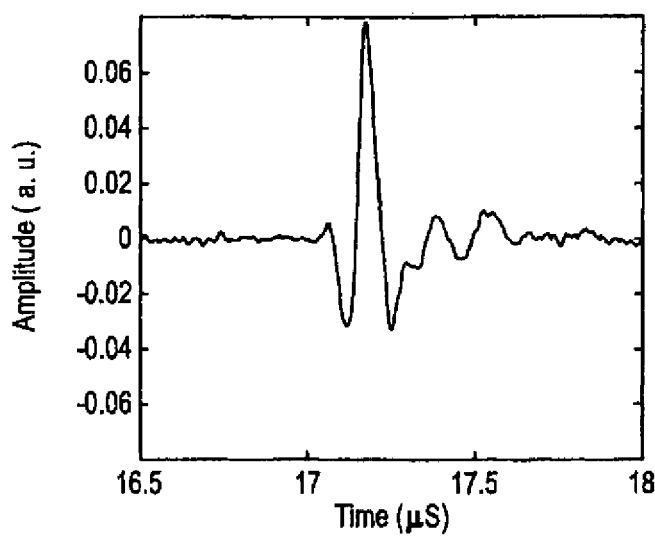
Figure 10B:
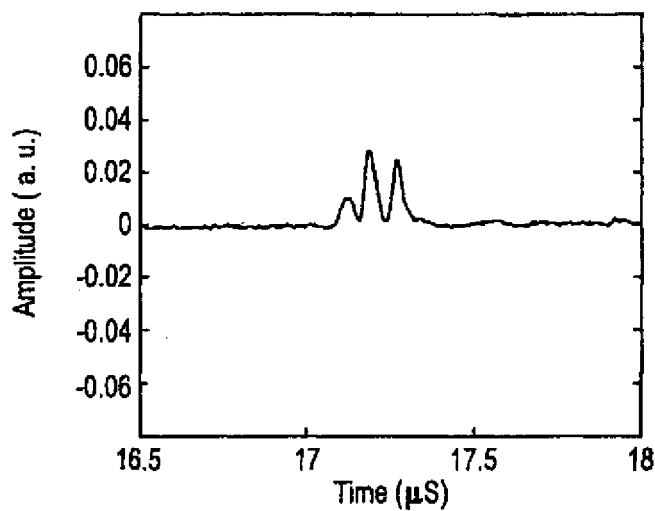
Figure 10C:
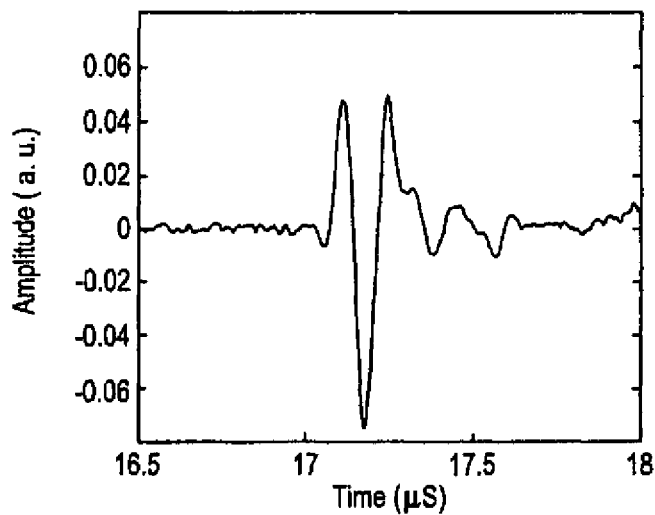
Figure 11A:
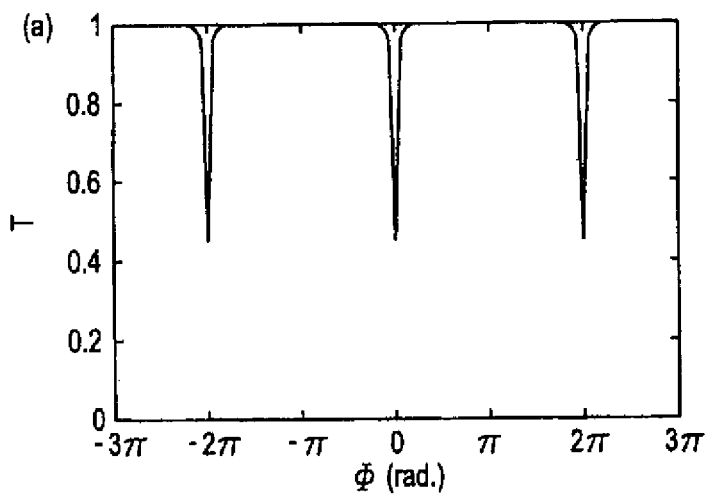
Figure 11B:
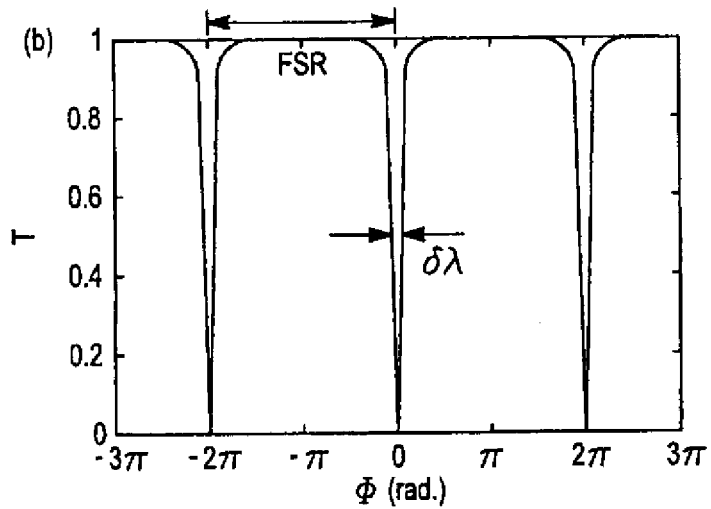
Figure 11C:
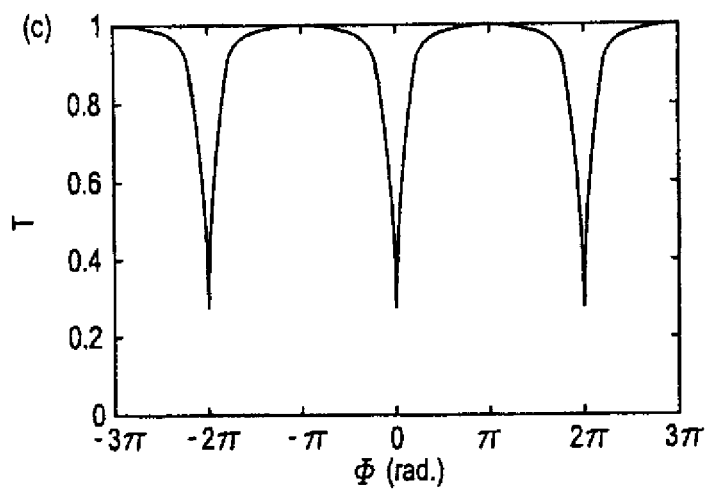
Figure 12A:
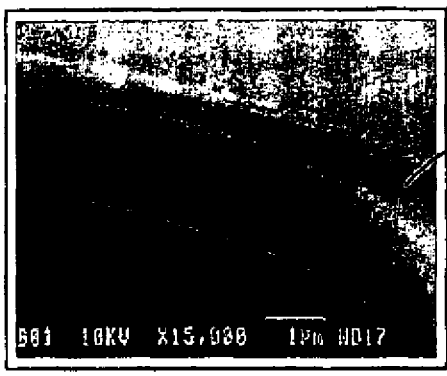
Figure 12B:
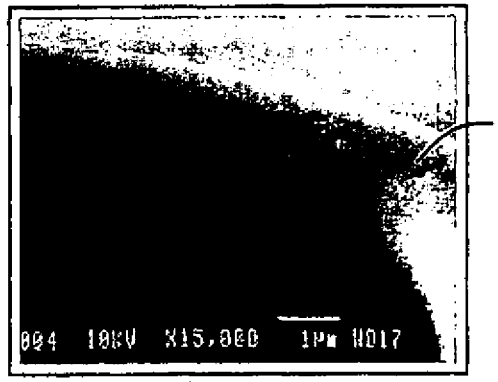
Figure 12C:
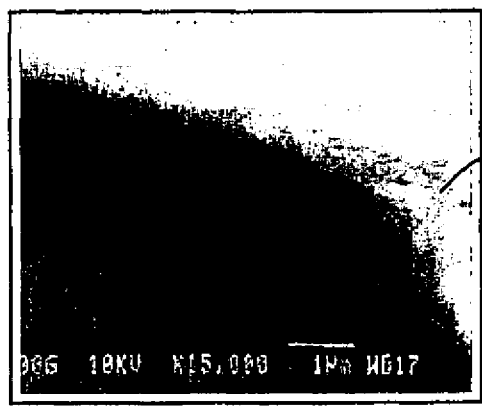
Figure 13:
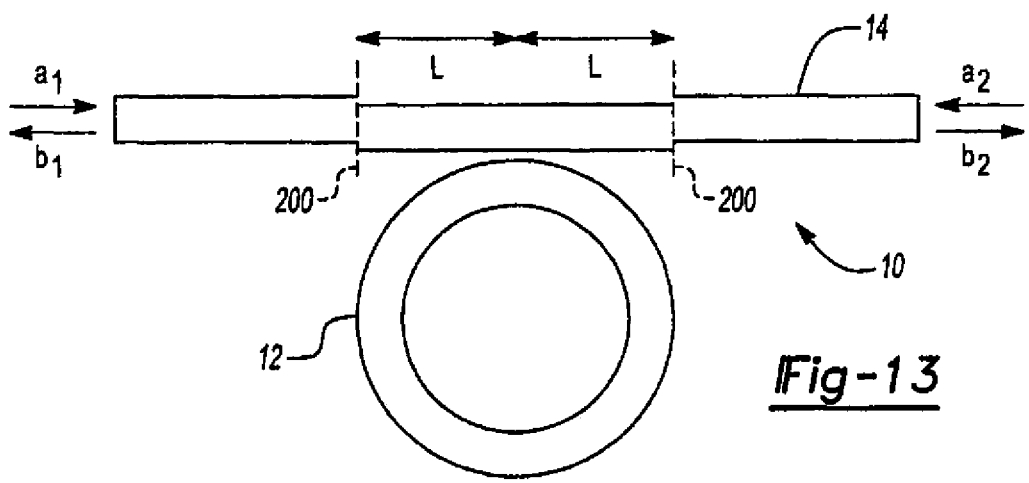
Figure 14:
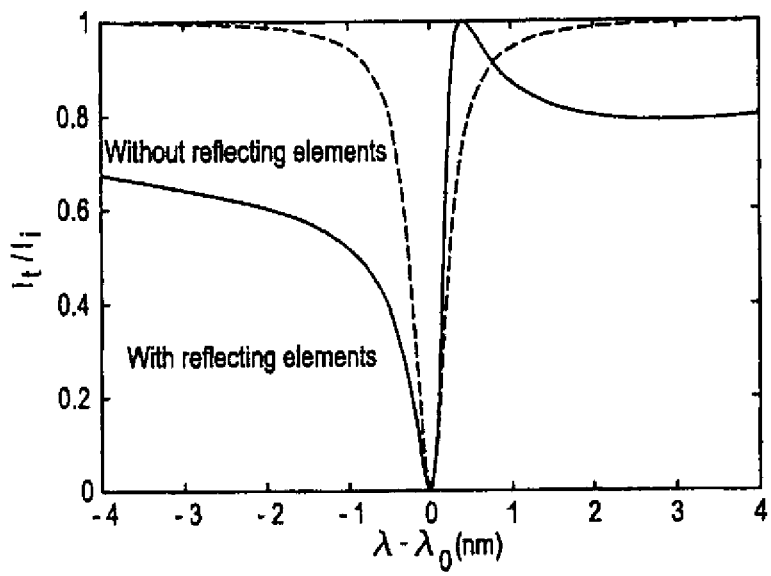
Figure 15:
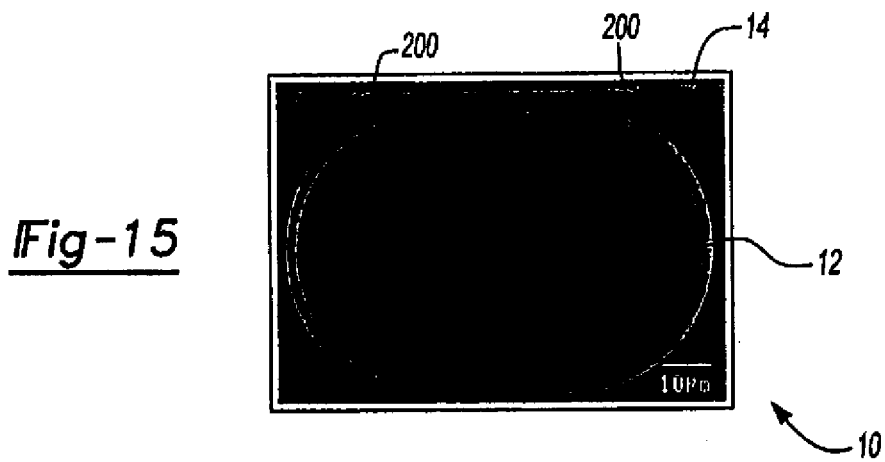
Figure 16:
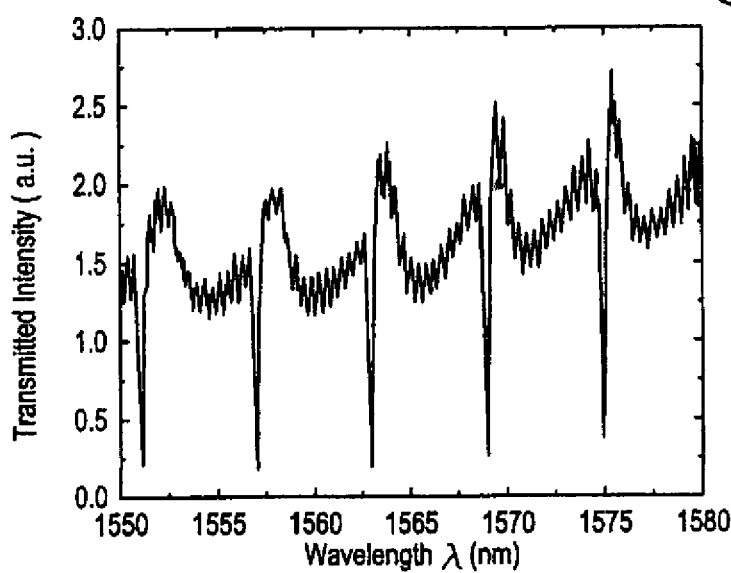
Figure 17:
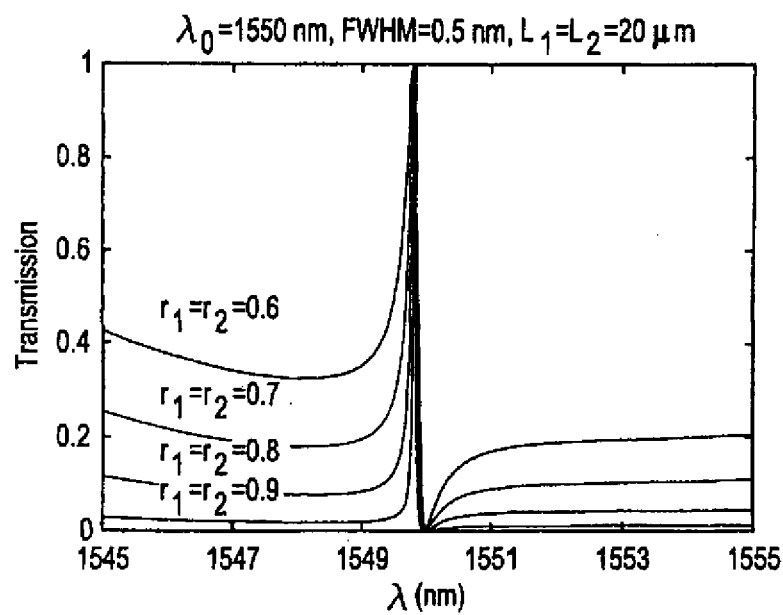
Figure 18:
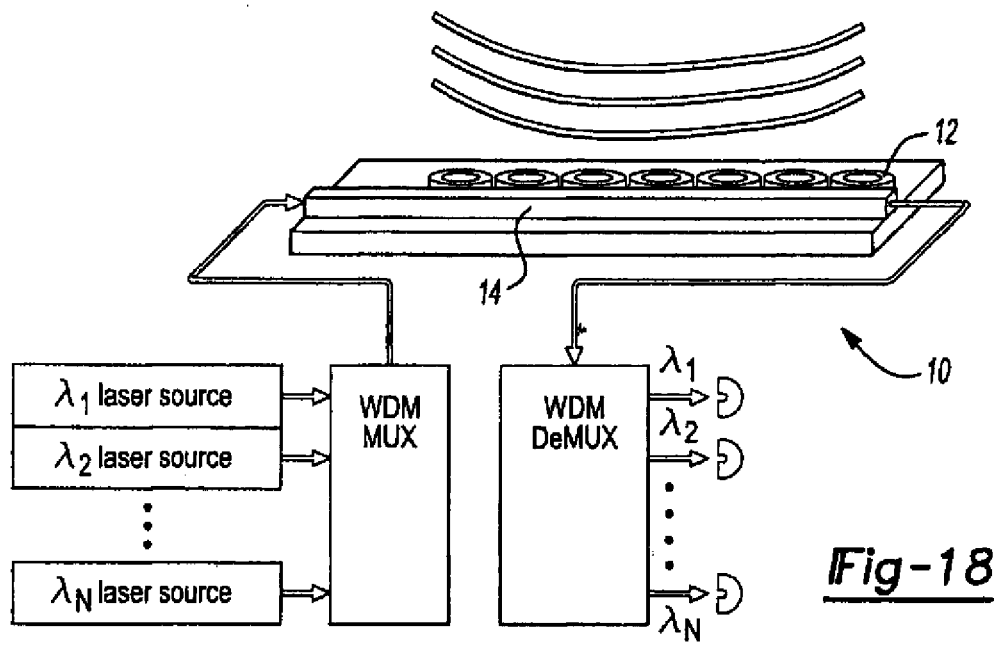

A direct imprinting technique can be used to fabricate such polymer waveguide resonators, which can be applied to a large number of polymer materials. In this technique, pattern replication is done by using a hard mold that contains nanoscale features defined on its surface to emboss into polymer material cast on the wafer substrate under controlled temperature and pressure. Nanoimprint has the capability of patterning sub-10 nm structures, which can produce the narrow and deep gap features in the microring devices. To this end, a mold is first fabricated by using a combination of electron-beam lithography, dry etching and nanoimprint. Next this mold is used to directly imprint into a thin polymer layer (e.g. polystyrene or PS) cast on a substrate ($SiO_2$ on Si) under pressure and at a temperature of 175° C., which is well above the glass transition temperature ($T_g$) of the polymer. After cool-down and de-molding, the residual polymer layer is removed, leaving polymer waveguides on top of $SiO_2$ (FIG. 5). A cross-section SEM picture of a typical polymer waveguide is shown in FIG. 6 (a wet etch is used in this case to create a pedestal structure for better mod confinement). FIG. 7(b) shows a typical spectrum of the fabricated PS microring devices measured from the drop port of the bus waveguide as shown in FIG. 5.

The acoustic sensitivity of the device was tested using a broadband ultrasonic transducer (Panametrics V311, 10 MHz, 12.5 mm diameter, 19 mm focal length) to insonify the microring waveguide. A pulser/receiver (Panametrics 5072PR) drove the ultrasound transducer. The transducer was coupled to the microring resonator using a horn shaped acrylic coupler filled with water based solid gel (SeaKem LE Agarose 2%, Cambrex BioSciences). The horn coupler was designed so that the focused acoustic radiation pattern is confined within the gel. This minimizes acoustic reflections from the acrylic walls of the coupler. The horn has an opening at the focal plane to couple acoustic radiation to the microring.

Figure 8:
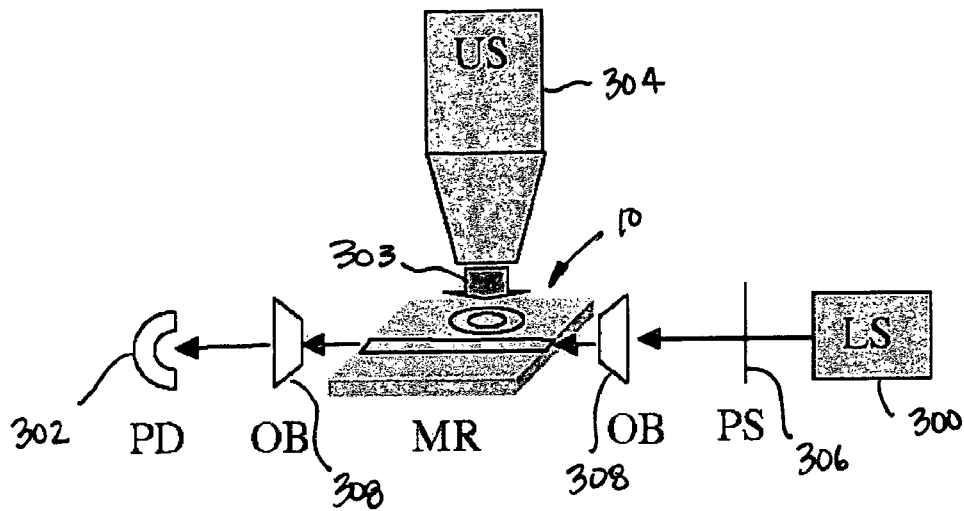
FIG. 8 is a schematic view illustrating an experimental set-up used for measuring the detection sensitivity of the microring resonator.

A schematic of the experimental setup is shown in FIG. 8. Microring resonator 10 was immersed in a liquid ultrasound coupling gel (Aquasonic100, Parker Laboratories Inc.) that served both as an optical cladding of the microring waveguide and acoustical coupling to the opening of the horn coupler. The output wavelength of a tunable laser 300 was set to a fixed wavelength near one of the resonance peaks (λ=1560.0 nm) which was selected after performing a fine scan of the resonance transmission curve (see FIG. 10(a)). The output power was set to 1.5 mW. A fast response amplified InGaAs photodiode (Newport 818-BB-30A) 302 was used to measure the transient response of the optical transmission following acoustic excitation 303 from an ultrasound pulse transmitter 304. The signal of the amplified photodiode was further amplified by the receiver within the pulser/receiver and recorded using a 400 MHz digital sampling oscilloscope (Tektronix TDS360). Polarizing optics 306 and objective lenses 308 were disposed between laser 300 and photodiode 302, as illustrated.

Figure 9:
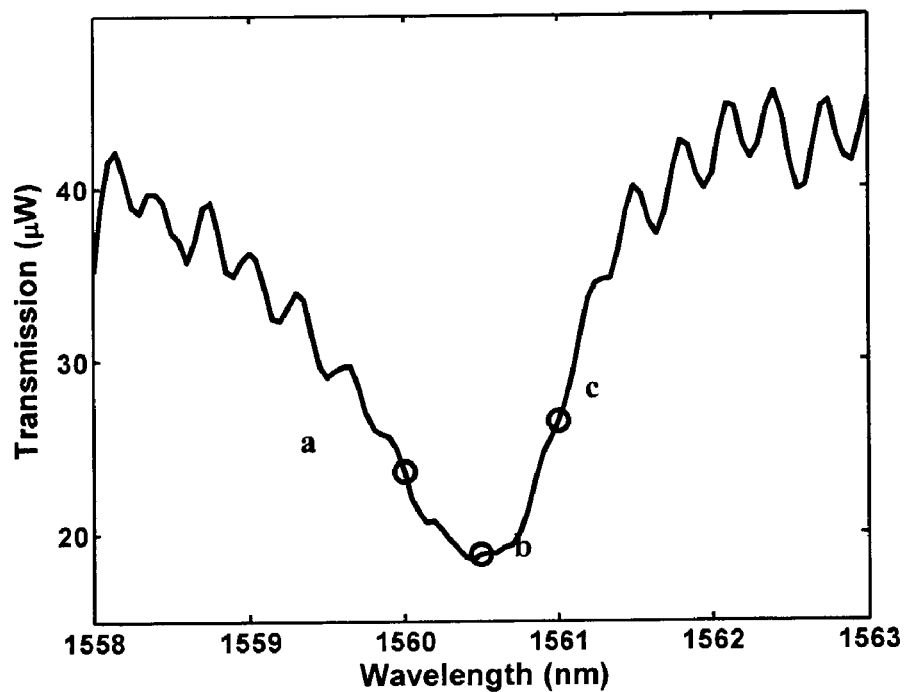
FIG. 9 is a graph illustrating a transmission spectrum of the microring device showing three wavelengths used in ultrasound modulation measurements.
Figure 10A:
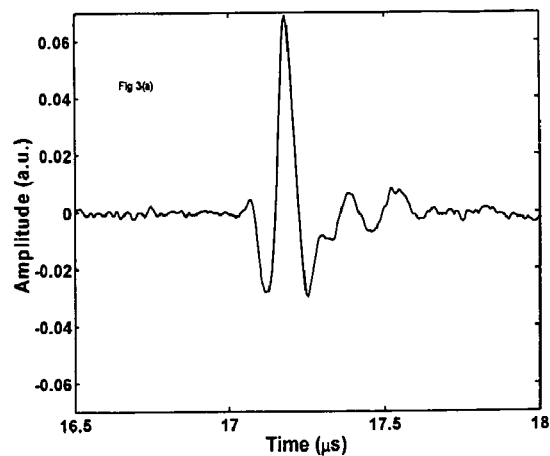
FIG. 10(a) is a graph illustrating the ultrasound modulated transmission signal at $\lambda=1560.0$ nm corresponding to Point a of FIG. 9.
Figure 10B:
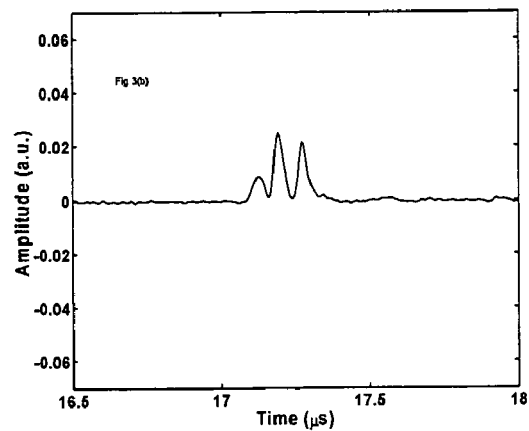
FIG. 10(b) is a graph illustrating the ultrasound modulated transmission signal at $\lambda=1560.5$ nm corresponding to Point b of FIG. 9.
Figure 10C:
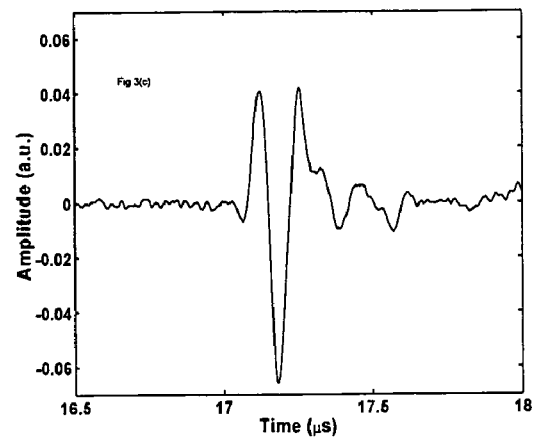
FIG. 10(c) is a graph illustrating the ultrasound modulated transmission signal at $\lambda=1561.0$ nm corresponding to Point c of FIG. 9.

A modulation signal was clearly observed following an acoustic propagation delay time (FIGS. 10(a)-(c)). The signal to noise ratio (SNR) of a single shot waveform was about 40. A clear illustration for the wavelength shift effect of the ultrasonic wave is obtained by observing the different signal response at three different wavelengths of excitation. In this regard, two of the wavelengths are located at the opposite sides of the resonance peak (see Points a and c in FIG. 9), while the third wavelength (see Point b in FIG. 9) was set to be close to the resonance peak. The excitation wavelength, in each case, is further marked as a vertical line on the insert of corresponding FIGS. 7(a)-(c). It is apparent that the signals corresponding to the two sides of the resonance peak have a linear response of opposite polarity, as expected due to sign change in the transmission slope. A dominant quadratic response is observed for the third signal (FIG. 10(b)) where the excitation wavelength corresponds to a minimum of the transmission spectrum (the resonance peak). The specific wavelength dependence of the response indicates that bulk effects, such as the mechanical displacement of the device under an ultrasound pulse, are not significant.

To evaluate the acoustic sensitivity of the device, the acoustic output was measured using a calibrated membrane PVDF hydrophone (GEC-Marconi Y-33-7611). The acoustic output was measured at the tip of the horn coupler within the focal zone of the acoustic radiation. The peak pressure at the maximal point was 64 KPa. The modulation of the optical transmission is assessed by normalizing the recorded waveform by the overall voltage gain and transimpedance gain, yielding a modulated optical power of 8.0 µW. Normalizing the modulation transmission power by the mean optical power reaching the detector gives a modulation depth of Tr=0.2. The measured sensitivity is therefore $D=Tr/Pa=3 \cdot 10^{-3}$ $KP_a^{-1}$. This value is much higher than the expected sensitivity due to straining of the microring waveguide, suggesting that different mechanisms may be responsible for the high sensitivity observed.

Figure 18:
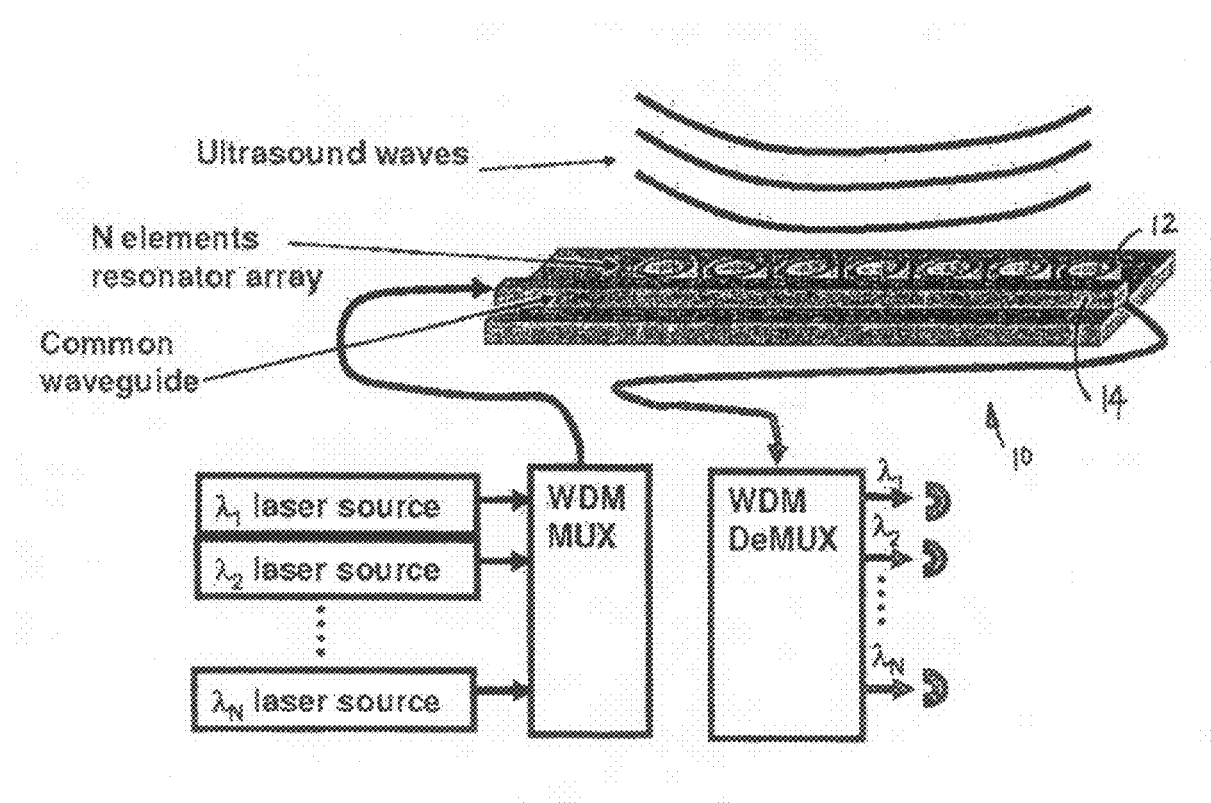
FIG. 18 is a schematic view illustrating a multi-element array ultrasonic receiver according to the principles of the present teachings.
Figure 1:
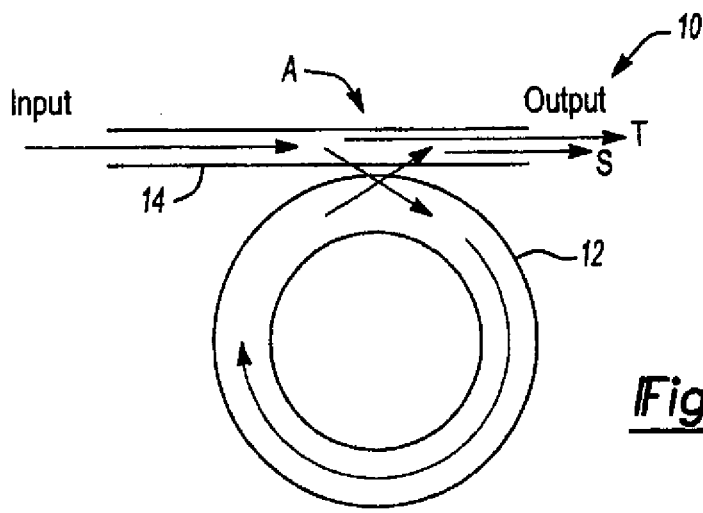
Figure 2:
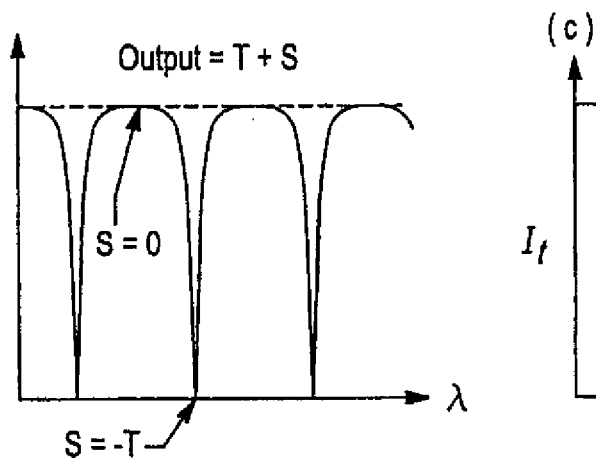
Figure 3:
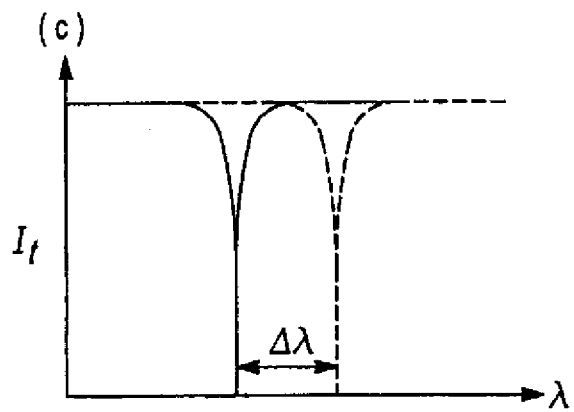
Figure 4:
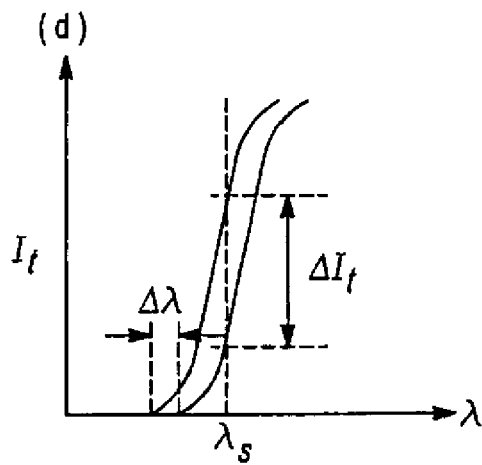

Therefore, a novel application of an optical microring resonator according to the present teaching can include a small (less than one acoustic wavelength) single element ultrasound receiver. The experimental characterization of the microring ultrasonic receiver shows high sensitivity and high bandwidth exceeding 10 MHz. The technique can be extended to realize a multi-element array ultrasonic receiver, using known techniques in the field of optical communication. Arrays of microring resonators can be used to operate as add-drop filter arrays for telecommunication applications, where multiple microring resonators (8 elements) are coupled to a common input bus waveguide and each has its own output waveguide. In this device, the ring radii can be changed with a fixed increment between each element and therefore each resonator can have a different resonance peak location. Coupling the light in the common bus waveguide to a specific output waveguide is achieved by choosing the appropriate wavelength. The same mechanism is applicable to the ultrasound receiver array where each element is addressed by selecting the appropriate wavelength at the input port, as seen in FIG. 18. Separate output waveguides for each element are not required in this case since the common bus waveguide can serve both as input and output ports. A 2-D array of N×M elements can be realized using N rows, where each row has M microring elements and its own bus waveguide.

The design of a 1-D or 2-D ultrasonic array using integrated optics device techniques offers unique advantages such as ruggedness, small size, RF immunity and low manufacturing cost, which could be beneficial in various ultrasound applications. A particularly appealing medical application is the design of a small integrated optical device which will operate as an intravascular imaging probe. The ultrasound pulse generator could be integrated using photoacoustic methods, therefore eliminating the need for any electrical cabling since fiber optics carry both input and output signals. The high element density required for high resolution intravascular imaging dictates an upper limit of 20 µm on the ring diameter. Reducing the size of the rings will also increase the free spectral range and therefore will increase the number of elements that can share a common bus waveguide. The drawback of small size rings is increased radiation loss, which may reduce the resonance Q-factor and therefore decrease sensitivity.

Methods

Physical Mechanism of Detecting Ultrasound Using Microring Resonator

It has been found that ultrasound waves impinging on a microring resonator induce modulations in its optical properties resulting in transmission modulations. Choosing a fixed excitation wavelength near the steep edge of the resonance peak greatly amplifies the optical response to the ultrasonic disturbance (see FIG. 4). Such response can occur as a result of strain induced by an ultrasound wave changing the effective refraction index of the optical waves propagating along the ring due to the geometric deformation in the cross-section of the ring waveguide. Additionally, such response can occur as a result ultrasound waves, which are density waves, modulating the polymer density thereby leading to change in the refraction index of the material. Still further, such response can occur as a result of similar density changes induced in the cladding material surrounding the waveguide and effectively modifying the effective refraction index of the guided mode. Finally, such response can occur as a result of ultrasound stress acting in the coupling region that modulates the coupling coefficient between the straight and the ring waveguides. Analysis of the relative contribution of each of the above effects indicated that the dominant effect is the straining of the waveguide cross-section, yet the measurements showed at least an order of magnitude higher sensitivity.

Microring Design Considerations

The sensitivity of a microring ultrasound detector is determined by the Q-factor of the microresonator. This can be seen easily since the resonance wavelength, $\lambda_c$, is determined from $n_{eff}L=m\lambda_c$, where $n_{eff}$ is the effective refractive index of the propagation mode, L the circumference of the microring, and m an integer. Small change in the effective index can be detected by measuring the resonance shift $\delta\lambda c$, and $\delta n_{eff}/n_{eff}=\delta\lambda_c/\lambda_c=1/Q$. Therefore, the minimum detectable effective index change is inversely proportional to the Q-factor of the device. In light of this, the resonator's Q-factor can be increased in a number of ways.

The resonance Q-factor is defined as the ratio of stored energy in the resonator cavity to the energy loss per cycle. In the case of a microring resonator, the energy loss is a result of various intrinsic losses in the microring waveguide, which determines $Q_{in}$; as well as the power coupling to the bus waveguide, which determines $Q_{ex}$. Therefore the net Q-factor of the resonator can be expressed as $Q^{-1}=Q_{ex}^{-1}+Q_{in}^{-1}$. The waveguide loss not only determines the $Q_{in}$, but also indirectly affects $Q_{ex}$. This is because in order to achieve large transmission contrast between on- and off-resonance, it is preferable to operate the device close to the critical coupling condition (a=|τ|). As can be seen from the calculated spectra of a microring coupled with a single bus waveguide (FIGS. 11(a)-(c)), the transmission at resonance reaches zero only at the critical coupling condition, where the fraction of field from the bus waveguide coupled to the microring (κ) is equal to the round-trip field attenuation in the microring (α), i.e. $\kappa=\kappa_c=\alpha$. If the coupling of power from bus waveguide to the microring is low ($\kappa<\kappa_c$), the microring is under-coupled; and if $\kappa>\kappa_c$ the resonator is over-coupled. In both latter cases, the resonance transmission cannot reach zero applications, leading to lower on-off contrast. Also in the over-coupled situation, the resonance linewidth is larger than that at critical coupling condition.

Since the waveguide loss is one of the most important factors that determines the overall resonance quality factor, it should be reduced in the device design and construction. For microring waveguide devices, intrinsic waveguide losses include radiation loss due to waveguide bending, leakage loss to the substrate, scattering loss due to surface roughness. It has been shown by previous experiments that the surface roughness induced scattering is the dominating loss mechanism in microfabricated ring and disk resonators.

Thermal Reflow Technique to Reduce Optical Scattering Loss

Figure 11A:
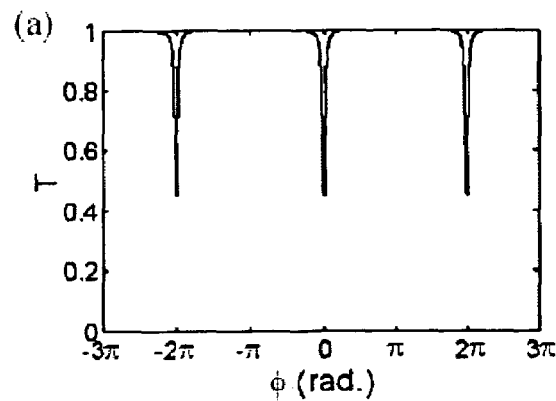
FIGS. 11(a)-(c) are graphs illustrating the calculated spectra of a single-coupled microring resonator with $\alpha_i=1$, $a=0.95$, and different $\tau$ values being $\tau=0.985$ (under-coupling); $\tau=0.95$ (critical-coupling); and $\tau=0.85$ (over-coupling), respectively.
Figure 11B:
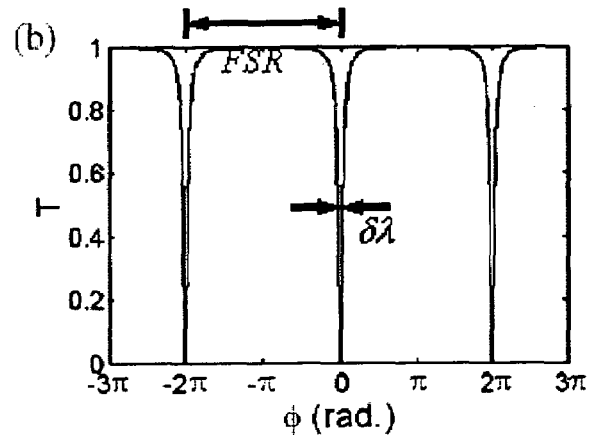
Figure 11C:
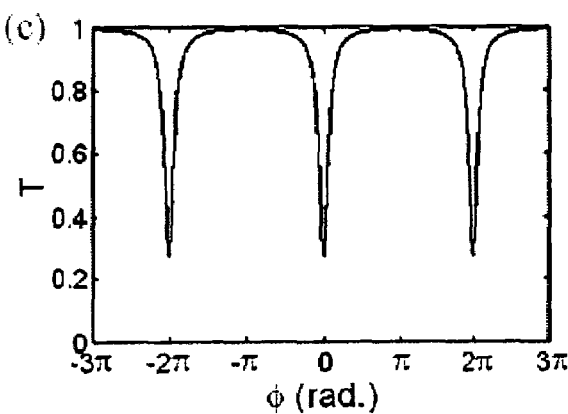
Figure 12A:
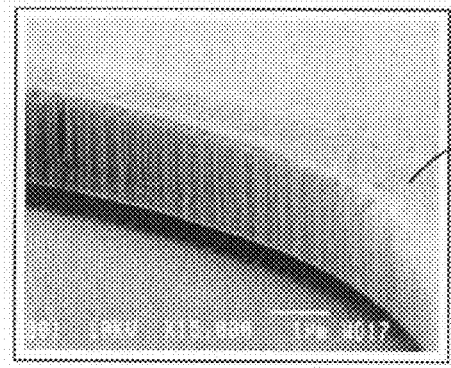
FIGS. 12(a)-(c) are SEM pictures of perspective views of the microring resonator without annealing, with annealing at 85° C. for 120 s, and with annealing at 95° C. for 60 s, respectively.
Figure 12B:
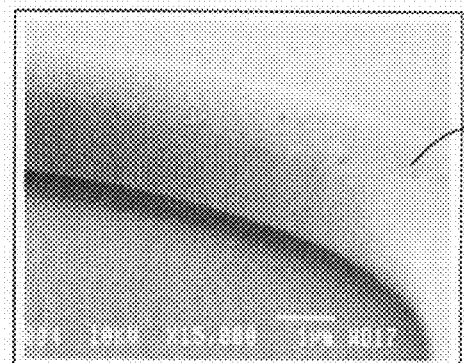
Figure 12C:
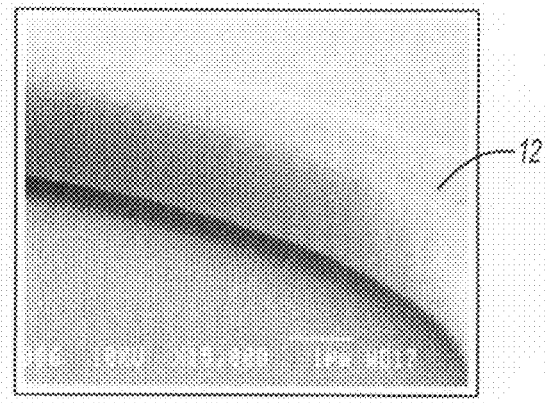

A simple thermal-reflow process to reduce the surface roughness of polymer waveguide can be used. This technique involves heating the fabricated polymer devices with controlled time duration in a temperature range of 10~20° C. below the $T_g$ of the polymer. By doing so, the viscosity of the material is reduced and its fluidity is enhanced. As a result, polymer structure can undergo reflow and the surface roughness can reduce significantly under the action of surface tension. These results were confirmed using an imprinted polystyrene microring device. SEM micrographs of PS microrings under different degrees of heat treatment are shown in FIGS. 11(a)-(c). The trend of improvement in surface smoothness can be clearly observed.

One critical issue of applying the thermal reflow technique to waveguide devices lies in the careful control of the temperature and time, while temperature being the most important factor. Because we have observed in our preliminary study that overheating or excessive long heating can change the cross-section of the waveguide dramatically from a rectangle to a mushroom shape. On the other hand, small and controlled waveguide deformation can also be exploited to our advantage, i.e. one can use the reflow technique to simultaneously reduce the gap distance in the coupling region of device, which could leverage the difficulty in producing the very narrow and high-aspect ratio gaps in the device fabrication. We also verified experimentally the effectiveness of this technique in reducing the surface roughness scattering by using the Fabry-Perot contrast method (or cut-back method). Preliminary study shows that using such a simple technique, the propagation loss in the imprinted polymer microring can be easily reduced by over 70 dB/cm. This method exploits the unique physical properties of polymer materials, and can be applied post device fabrication to fine tune the device performance, which offers a great advantage than ring resonators made in semiconductors and dielectric materials. With the aid of this technique, a total round trip loss to below 5 dB/cm, which is over an order of magnitude lower than most of the reported microring devices, can be achieved.

Optimizing Q Factor—Fano Resonators

In microrings having a diameter of about 15 µm, the size of the microring may cause radiation loss due to the sharp bending of the waveguide. If this loss becomes significant in determining the attainable Q factor, the present teachings provide a design scheme to increase the device sensitivity by exploiting a sharp asymmetrical Fano-resonance.

Figure 13:
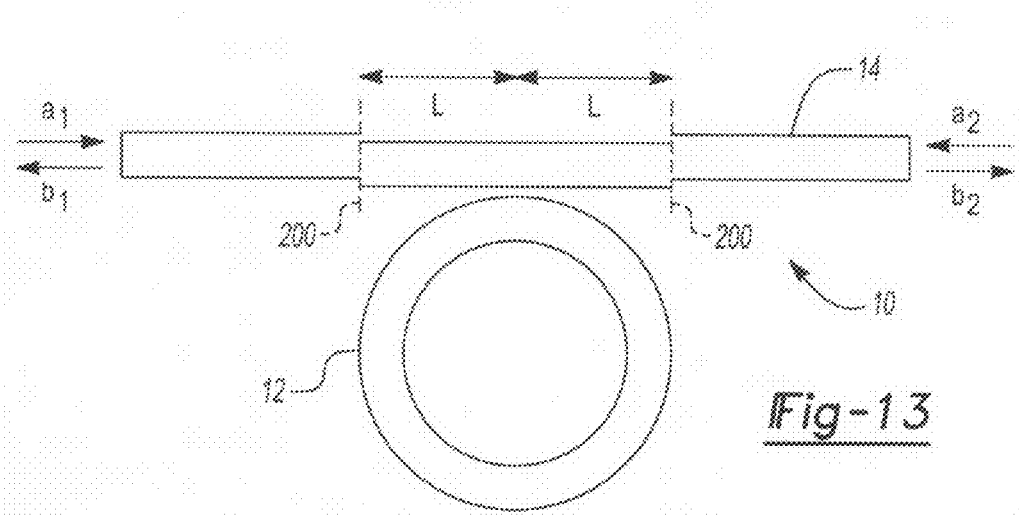
FIG. 13 is a schematic view illustrating a microring resonator having reflecting elements according to the principles of the present teachings.
Figure 14:
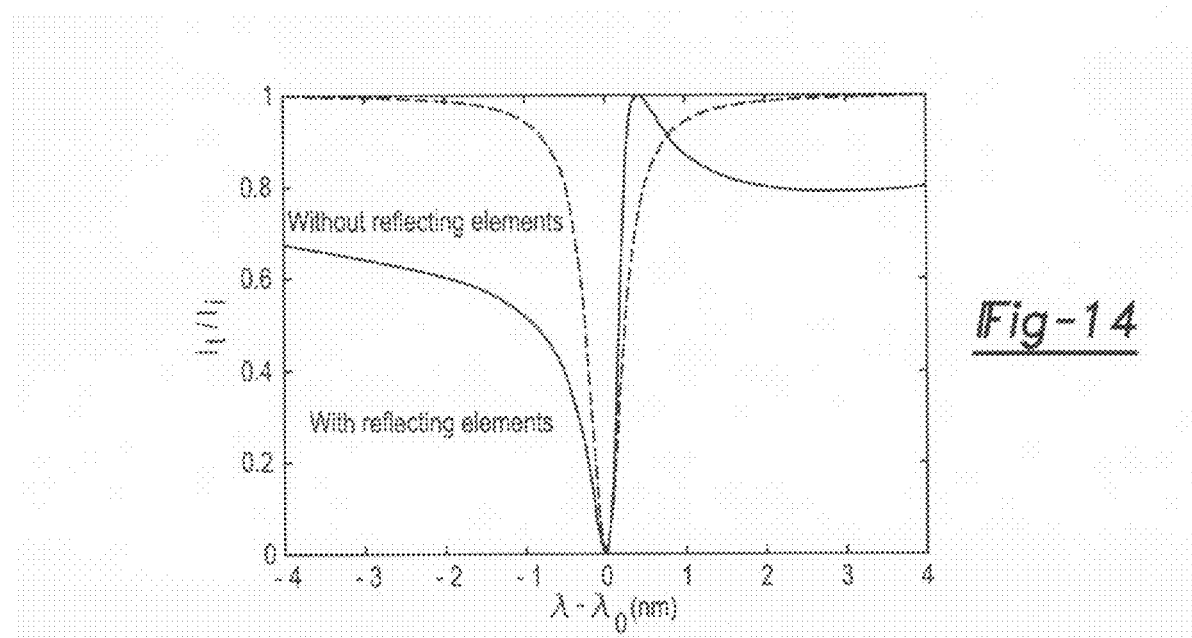
FIG. 14 is a graph illustrating simulated transmission spectra of a microring with and without reflecting elements.

The resonance line-shape of a traditional microring or microsphere resonator is symmetrical with respect to its resonant wavelengths (dotted line of FIG. 14). However, according to the present teachings, a new resonator structure can be used that incorporates two partially reflecting elements in the bus waveguide (FIG. 13). In the present development, an asymmetric Fano-resonance line shape has been found that can have significantly increased slope between full and zero transmissions. An example of such an asymmetric resonance is shown in FIG. 14 (solid line). For the detector application of the present teachings, the sharply asymmetric line-shape of the Fano-resonance can provide higher slope sensitivity than conventional microring structures made with the same Q-factor.

Figure 15:
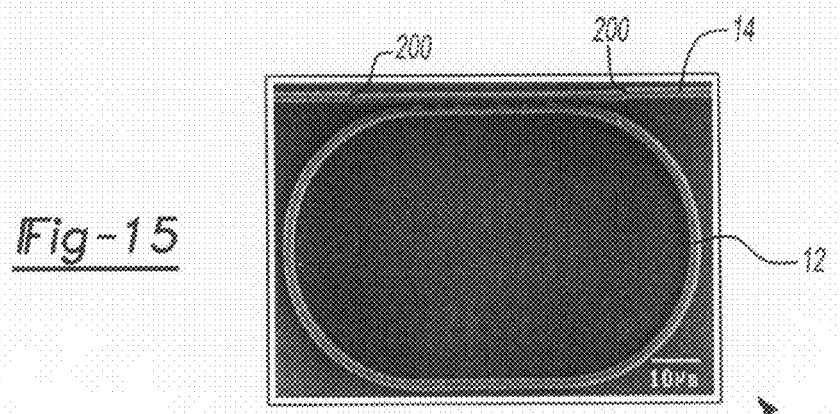
FIG. 15 is a SEM picture of a plan view of the microring resonator with reflecting elements.
Figure 16:
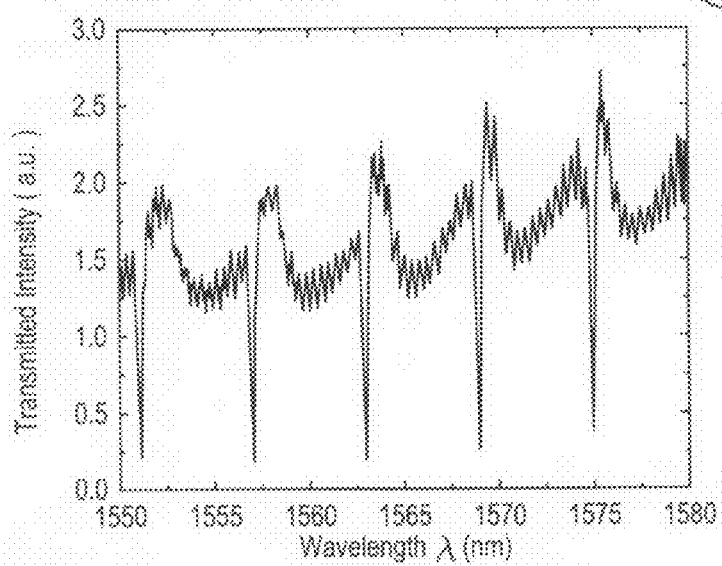
FIG. 16 is a graph illustrating the measured transmission spectrum showing the Fano-resonance-like behavior.

Referring now to FIG. 13, the microring structure of the present teachings includes two partial reflecting elements 200 that are achieved by waveguide offsets. The magnitude of the offset controls the reflection and affects the line shape of the calculated transmission spectrum, as seen in FIG. 14. Turning now to FIG. 15, a scanning electron micrograph of such a device is illustrated. As seen in FIG. 16, the measured transmission spectrum of such a device is provided that clearly shows the asymmetric Fano-resonance line shape. This increased slope has been exploited by using the device to detect the concentration of glucose in an aqueous solution.

Figure 17:
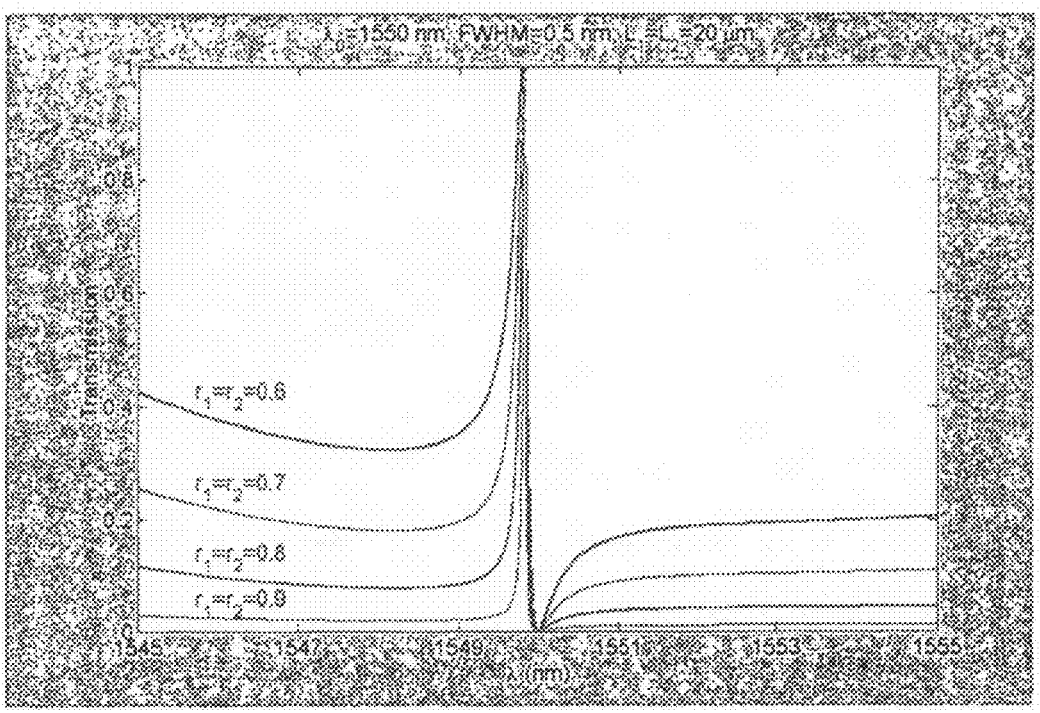
FIG. 17 is a graph illustrating various Fano-resonance line shapes achieved by different degrees of reflection.

It has been found that the Fano-resonance line shapes can be changed dramatically by controlling the position of the reflecting elements and the reflection coefficients, and very sharp resonances can be obtained (FIG. 17). High-Q resonance can be achieved with highly reflective elements placed in the bus waveguide, despite of the various loss factors in the microresonator. The reason may be that such reflecting elements create a high finesse Fabry-Perot resonator, which couples with the microring resonator. It is anticipated that using this approach, polymer microring resonators can be developed with extraordinary high-Q factors, which will results in compact and highly-sensitive ultrasound detectors.

The description of the teachings is merely exemplary in nature and, thus, variations that do not depart from the gist of the teachings are intended to be within the scope of the teachings. Such variations are not to be regarded as a departure from the spirit and scope of the teachings.

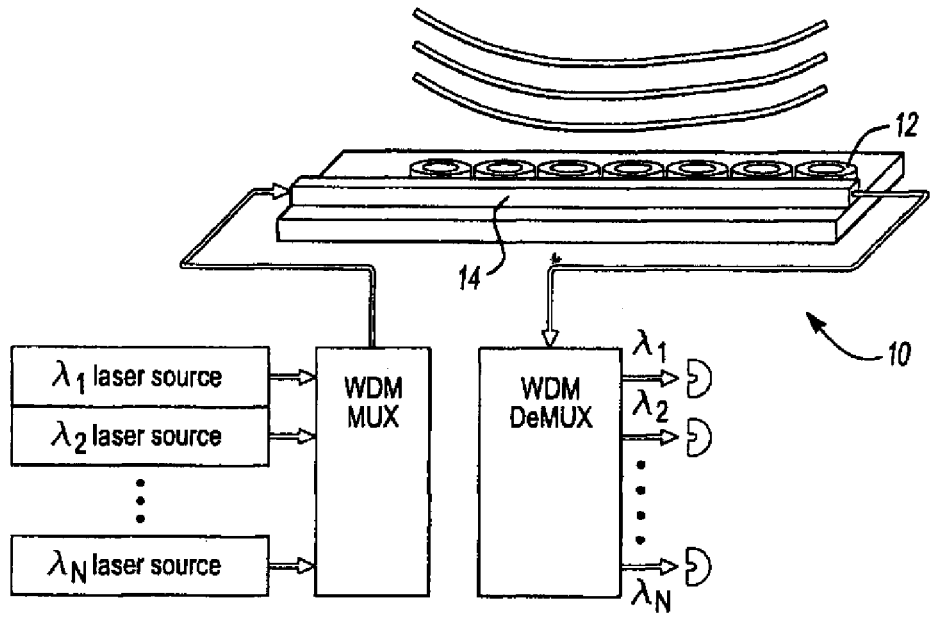

What is claimed is:

1. A method of detecting an acoustic waves comprising:
   providing a resonator device having a straight waveguide and a closed-loop waveguide, said closed-loop waveguide defining a first cross-section;
   irradiating said resonator device with acoustic waves thereby imparting a strain on said closed-loop waveguide, said strain causing said closed-loop waveguide to deform to a second cross-section thereby changing from a first effective refractive index to a second effective refractive index, said second cross-section being different than said first cross-section;
   transmitting a signal within said resonator device from an input end to an output end, said signal from said output end being varied in response to said irradiating said resonator device with acoustic waves; and
   analyzing said signal transmitted within said resonator device to detect a predetermined property of the acoustic waves.

2. The method according to claim 1 wherein said providing a resonator device having a straight waveguide and a closed-loop waveguide comprises:
   providing a resonator device having a straight waveguide, a closed-loop waveguide, and a pair of partially reflecting elements disposed in said straight waveguide.

3. The method according to claim 1 wherein said providing a resonator device comprises:
   annealing at least a portion of said resonator device to provide reduced surface roughness thereof.

4. The method according to claim 1, further comprising:
   a plurality of said resonator devices arranged in an array, each of said plurality of resonator device detecting one or more predetermined acoustic waves.

5. The method according to claim 1, further comprising:
   a plurality of said resonator devices arranged in an array, each of said plurality of resonator device operates at different resonance wavelengths detecting one or more predetermined acoustic waves.

6. The method according to claim 1 wherein said irradiating said resonator device with acoustic waves comprises irradiating said resonator device with an ultrasound.

7. The method according to claim 1 wherein said providing a resonator device having a straight waveguide and a closed-loop waveguide comprises providing a resonator device having a straight waveguide and a closed-loop waveguide selected from the group consisting of a microring, a disc, a rectangle, and a sphere.

8. The method according to claim 1 wherein said providing a resonator device having a straight waveguide and a closed-loop waveguide comprises providing a resonator device having a straight waveguide and a closed-loop waveguide being spaced apart a predetermined distance, said predetermined distance remaining unchanged during said irradiating said resonator device with acoustic waves.

9. A method of detecting an ultrasound waves comprising:
providing a resonator device having an optical waveguide having an input portion and an output portion and a microring coupled to said optical waveguide, said microring defining a first cross-section resulting in a first effective refractive index;
providing a pair of partially reflecting elements disposed in said optical waveguide;
irradiating said resonator device with ultrasound waves thereby imparting a strain on said microring, said strain causing said microring to deform to a second cross-section resulting in a second effective refractive index, said second effective refractive index being different than said first effective refractive index;
transmitting a signal within said resonator device from an input end to an output end, said signal from said output end being varied in response to said irradiating said resonator device with ultrasound waves; and
analyzing said signal transmitted within said resonator device to detect a predetermined property of the ultrasound waves.

10. The method according to claim 9 wherein said providing a resonator device comprises:
annealing at least a portion of said resonator device to provide reduced surface roughness thereof.

11. The method according to claim 9, further comprising:
a plurality of said resonator devices arranged in an array, each of said plurality of resonator device detecting one or more predetermined ultrasound waves.

12. The method according to claim 9, further comprising:
a plurality of said resonator devices arranged in an array, each of said plurality of resonator device operates at different resonance wavelengths detecting one or more predetermined ultrasound waves.

13. A method of detecting an ultrasound waves comprising:
providing a resonator device having at least one straight waveguide having an input portion and an output portion and a plurality of closed-loop waveguides coupled to said straight waveguide, each of said plurality of closed-loop waveguides defining a different resonant optical wavelength and having a first cross-section resulting in a first effective refractive index;
irradiating said resonator device with acoustic waves thereby imparting a strain on each of said plurality of closed-loop waveguides, said strain causing said plurality of closed-loop waveguides to deform to a second cross-section resulting in each having a second effective refractive index, said second effective refractive index being different than said first effective refractive index;
transmitting a signal within said resonator device from an input end to an output end, said signal from said output end being varied in response to said irradiating said resonator device with acoustic waves; and
analyzing said signal transmitted within said resonator device to detect a predetermined property of the ultrasound waves.

14. The method according to claim 13 wherein said transmitting a signal comprises transmitting one or more signals selectively corresponding to each of said different resonant optical wavelengths.

15. The method according to claim 14 wherein said transmitting one or more signals comprises transmitting said one or more signals simultaneously.

16. method according to claim 14 wherein said transmitting one or more signals comprises transmitting said one or more signals such that one of said plurality of closed-loop waveguides is addressed at a single time.

17. method according to claim 13 wherein said providing a resonator device further comprises:
providing a pair of partially reflecting elements disposed in said straight waveguide.

18. method according to claim 13 wherein said providing a resonator device comprises:
annealing at least a portion of said resonator device to provide reduced surface roughness thereof.

19. method according to claim 13, further comprising:
a plurality of said resonator devices arranged in an array, each of said plurality of resonator device detecting one or more predetermined ultrasound waves.

20. An acoustic wave detector comprising:
an optical waveguide having an input portion and an output portion; and
an optical resonator coupled to said optical waveguide,
wherein acoustic waves irradiating said optical resonator induce a strain modifying a cross-sectional profile of said optical resonator resulting in a change of an effective refractive index of said optical waveguide such that a signal passed therethrough varies in response to said modification of said effective refractive index; and
means for analyzing said signal transmitted within said optical resonator to detect a predetermined property of the acoustic waves.

21. The acoustic wave detector according to claim 20, further comprising:
a pair of partially reflecting elements disposed in said optical waveguide.

22. The acoustic wave detector according to claim 20 wherein said optical resonator is a microring.

23. The acoustic wave detector according to claim 20 wherein said optical resonator is a disc.

24. The acoustic wave detector according to claim 20 wherein said optical resonator is a rectangular device.

25. The acoustic wave detector according to claim 20 wherein said optical resonator is a sphere.

26. An acoustic wave detector comprising:
a plurality of optical waveguides each having an input portion and an output portion;
a plurality of optical resonators each coupled to a respective one of said plurality of optical waveguides,
wherein acoustic waves irradiating said optical resonators induce a strain modifying a cross-sectional profile of each of said plurality of optical resonators resulting in a change of an effective refractive index of said optical waveguide and vary a signal transmitted therethrough; and
means for analyzing said signal transmitted within said plurality of optical resonators to detect a predetermined property of the acoustic waves.

* * * * *

UNITED STATES PATENT AND TRADEMARK OFFICE
CERTIFICATE OF CORRECTION

PATENT NO. : 7,587,105 B2
APPLICATION NO. : 11/662154
DATED : September 8, 2009
INVENTOR(S) : Shai Ashkenazi et al.

It is certified that error appears in the above-identified patent and that said Letters Patent is hereby corrected as shown below:

Column Title Page (57), Abstract, "a optical" should be --an optical--.

Title page, illustrative fig. 18 should be deleted and substitute therefore the attached title page consisting of illustrative fig. 18.

In the Drawings

The drawing sheets 1-8 consisting of Fig(s) 1-18 should be deleted and substitute therefore the attached drawing sheets 1-8 consisting of Fig(s) 1-18.

Column 1, lines 60-61, "micror-ing" should be --micro-ring--.

Column 2, lines 3-4, "micros-copy" should be --micro-scopy--.

Column 2, line 29, after "better", insert --than--.

Column 2, line 32, "relying" should be --relies--.

Column 3, line 2, "chance" should be --change--.

Column 5, line 57, "Resonance" should be --resonance--.

Column 6, lines 35-36, "micror-ing" should be --micro-ring--.

Column 8, lines 36-37, "micror-ing" should be --micro-ring--.

Column 10, lines 6-7, "Micror-ing" should be --Micro-ring--.

Column 10, line 18, after "result", insert --of--.

Column 10, line 39, "$\delta\lambda c$" should be --$\delta\lambda_c$--.

Signed and Sealed this

Twenty-ninth Day of June, 2010

David J. Kappos
*Director of the United States Patent and Trademark Office*

Column 11, line 34, after "of", insert --the--.

Column 11, line 45, "great" should be --greater--.

Column 12, line 19, after "despite", delete "of".

Column 12, line 24, after "which", delete "will".

Column 12, line 32, claim 1, after "detecting", delete "an".

Column 12, line 61, claim 4, "device" should be --devices--.

Column 12, line 66, claim 5, "device" should be --devices--.

Column 13, line 16, claim 9, after "detecting", delete "an".

Column 13, line 42, claim 11, "device" should be --devices--.

Column 13, line 46, claim 12, "device" should be --devices--.

Column 13, line 49, claim 13, after "detecting", delete "an".

Column 14, line 13, claim 16, before "method", insert --The--.

Column 14, line 16, claim 17, before "method", insert --The--.

Column 14, line 20, claim 18, before "method", insert --The--.

Column 14, line 24, claim 19, before "method", insert --The--.

Column 14, line 26, claim 19, "device" should be --devices--.

(12) United States Patent
Ashkenazi et al.

(10) Patent No.: US 7,587,105 B2
(45) Date of Patent: Sep. 8, 2009

(54) HIGH FREQUENCY ULTRASOUND DETECTION USING POLYMER OPTICAL-RING RESONATOR

(75) Inventors: Shai Ashkenazi, Ann Arbor, MI (US); Lingjie Jay Guo, Ann Arbor, MI (US); Matthew O'Donnell, Ann Arbor, MI (US)

(73) Assignee: The Regents Of The University Of Michigan, Ann Arbor, MI (US)

( * ) Notice: Subject to any disclaimer, the term of this patent is extended or adjusted under 35 U.S.C. 154(b) by 23 days.

(21) Appl. No.: 11/662,154

(22) PCT Filed: Sep. 8, 2005

(86) PCT No.: PCT/US2005/031905

§ 371 (c)(1),
(2), (4) Date: Mar. 7, 2007

(87) PCT Pub. No.: WO2007/018552

PCT Pub. Date: Feb. 15, 2007

(65) Prior Publication Data

US 2008/0095490 A1     Apr. 24, 2008

Related U.S. Application Data

(60) Provisional application No. 60/607,982, filed on Sep. 8, 2004.

(51) Int. Cl.
*G02B 6/00* (2006.01)
(52) U.S. Cl. ............................................. 385/13
(58) Field of Classification Search .............. 385/7, 385/13, 30, 32, 50
See application file for complete search history.

(56) References Cited

U.S. PATENT DOCUMENTS 5,091,983 A * 2/1992 Lukosz ................ 385/13
7,526,148 B2 * 4/2009 Kilic et al. ............ 385/12

* cited by examiner

*Primary Examiner*—Sarah Song
(74) *Attorney, Agent, or Firm*—Harness, Dickey & Pierce, P.L.C.

(57) ABSTRACT

A polymer waveguide resonator device for high-frequency ultrasound detection having a optical resonator coupled to a straight optical waveguide which serves as input and output ports. Acoustic waves irradiating the waveguide induce strain modifying the waveguide cross-section or other design property. As a consequence, the effective refractive index of optical waves propagating along the ring is modified. The sharp wavelength dependence of the high Q-factor resonator enhances the optical response to acoustic strain. High sensitivity is demonstrated experimentally in detecting broadband ultrasound pulses from a 10 MHz transducer.

26 Claims, 8 Drawing Sheets